United States Patent [19]

Logan

[11] Patent Number: 4,755,680

[45] Date of Patent: Jul. 5, 1988

[54] RADIATION IMAGING APPARATUS AND METHODS

[75] Inventor: K. William Logan, Columbia, Mo.

[73] Assignee: The Curators of the University of Missouri, Columbia, Mo.

[21] Appl. No.: 604,989

[22] Filed: Apr. 27, 1984

[51] Int. Cl.[4] .............................................. G01T 1/164
[52] U.S. Cl. .................................. 250/363 R; 250/369
[58] Field of Search .................... 250/363 S, 369, 366; 364/414

[56] References Cited

U.S. PATENT DOCUMENTS

| | | | |
|---|---|---|---|
| 3,919,556 | 1/1975 | Berninger | 250/366 |
| 3,970,853 | 7/1976 | Kuhl et al. | 250/363 S |
| 4,071,769 | 1/1978 | Brunnett et al. | |
| 4,095,107 | 6/1978 | Genna et al. | 250/363 S |
| 4,095,108 | 6/1978 | Inbar et al. | 250/369 |
| 4,109,150 | 8/1978 | Martone et al. | 250/368 |
| 4,181,839 | 1/1980 | Hatton et al. | 250/505 |
| 4,197,460 | 4/1980 | Anger | 250/363 S |
| 4,213,054 | 7/1980 | Doherty, III | 250/505 |
| 4,228,515 | 10/1980 | Genna et al. | 364/571 |
| 4,289,965 | 9/1981 | Koga et al. | 250/363 S |
| 4,321,472 | 3/1982 | Cushman | 378/38 |
| 4,389,569 | 6/1983 | Hattori et al. | 250/363 S |
| 4,531,058 | 7/1985 | Burnham et al. | 250/366 |
| 4,584,478 | 4/1986 | Genna et al. | 250/363 SB |

FOREIGN PATENT DOCUMENTS 58-14071  1/1983  Japan ............................ 250/363 SA

OTHER PUBLICATIONS

Burnham et al, "One Dimensional Scintillation Cameras for Positron ECT Ring Detectors", IEEE Trans. Nuc. Sci, 28 (1), Feb. 1981, pp. 109-113.

Webster's New Collegiate Dictionary, G. & C. Merriam Co., 1977, p. 46.

McGraw Hill Dictionary of Scientific and Technical Terms, face sheet and p. 82.

Webster's Third New International Dictionary, face sheets and p. 88.

R. L. Richardson, "Anger Scintillation Camera", in Nuclear Medicine Physics, Instrumentation, and Agents, F. D. Rollo, ed., 1977, pp. 231-270, C. V. Mosby Co., St. Louis.

S. Genna et al., "Analysis of an Arcuate Gamma Camera Design for Transaxial Reconstruction", in *Medical Radionuclide Imaging*, 1977, pp. 323-339, International Atomic Energy Agency, Vienna.

S. Genna et al., "Application of Fan Reconstruction Geometries to Transmission and Emission Systems", in *Workshop on Reconstruction Tomography in Diagnostic Radiology and Nuclear Medicine*, M. M. Ter-Pogossian, ed., 1977, pp. 139-154, University Park Press, Baltimore, Md.

S. Genna et al., "Analysis of Resolution and Uniformity Characteristics of A Digital Camera", 1978 (abstract from 64th assembly, Radiological Society of North America).

(List continued on next page.)

*Primary Examiner*—Carolyn E. Fields
*Attorney, Agent, or Firm*—Senniger, Powers, Leavitt and Roedel

[57] ABSTRACT

Radiation imaging apparatus includes a substantially tubular body of material capable of producing scintillations in response to bombardment by ionizing radiation and means for converting the scintillations to electrical outputs including a plurality of scintillation sensing units disposed both along and around the outside of the substantially tubular body. A radiation imaging method processes outputs of the scintillation sensing units, which have axial positions and positions relative to first and second coordinates perpendicular to a longitudinal axis of the tubular body. The steps include computing in electrical form a first weighted sum of the outputs of units, the output of each unit being weighted in the sum depending on its position relative to the first coordinate, computing in electrical form a second weighted sum of the outputs of the units, the output of each unit being weighted in the second sum depending on its position relative to the second coordinate, and computing in electrical form a value of position for at least one of the scintillations as a function of the first and second weighted sums for the first and second coordinates.

92 Claims, 13 Drawing Sheets

OTHER PUBLICATIONS

S. Genna et al., "Digital Scintigraphy: Principles, Design, and Performance", *Journal of Nuclear Medicine*, vol. 22, No. 4, 1981, pp. 365-371.

Y. Hirose et al., "A Hybrid Emission CT-Headtome II", *IEEE Trans. Nuclear Science*, vol. NS-29, No. 1, 1982, pp. 520-523.

A. Rosenfeld et al., *Digital Picture Processing*, 2nd ed., vol. 1, 1982, pp. 353-427, Academic Press, N.Y.

Genna et al. "Digital Scintigraphy: Concepts and Designs" *IEEE Trans. Nuc. Sci.*, vol. NS-29, No. 1, 2/82, pp. 558-562.

Burnham et al. "A Positron Tomograph Employing a One Dimension BGO Scintillation Camera" *IEEE Trans. Nuc. Sci.* vol. NS-30, No. 1, Feb. 1983, pp. 661-664.

Cho et al., "Performance of Single Photon Tomographic System-GAMMATOM-1" *IEEE Trans. Nuc. Sci.*, vol. NS-29, No. 1, Feb. 1982, pp. 484-487.

Ricci et al. "Investigation of a Technique for Providing a Pseudo-continuous Detector Ring for Positron Tomography" *IEEE Trans. Nuc. Sci.*, vol. NS-29, No. 1, Feb. 1982, pp. 452-456.

McIntyre "Design Features of a Positron Tomograph with 2.4 mm Resolution" *IEEE Trans. Nuc. Sci.*, vol. NS-27, No. 4, Aug. 1980, pp. 1305-1311.

Muehllehner et al. "Use of Position Sensitive Detectors in Positron Imaging" *IEEE Trans. Nuc. Sci.*, vol. NS-27, 1980, pp. 569-571.

Muehllehner et al. "Performance Parameters of a Positron Imaging Camera" *IEEE Trans. Nuc. Sci.*, vol. NS-23, No. 1, Feb. 1976, pp. 528-537.

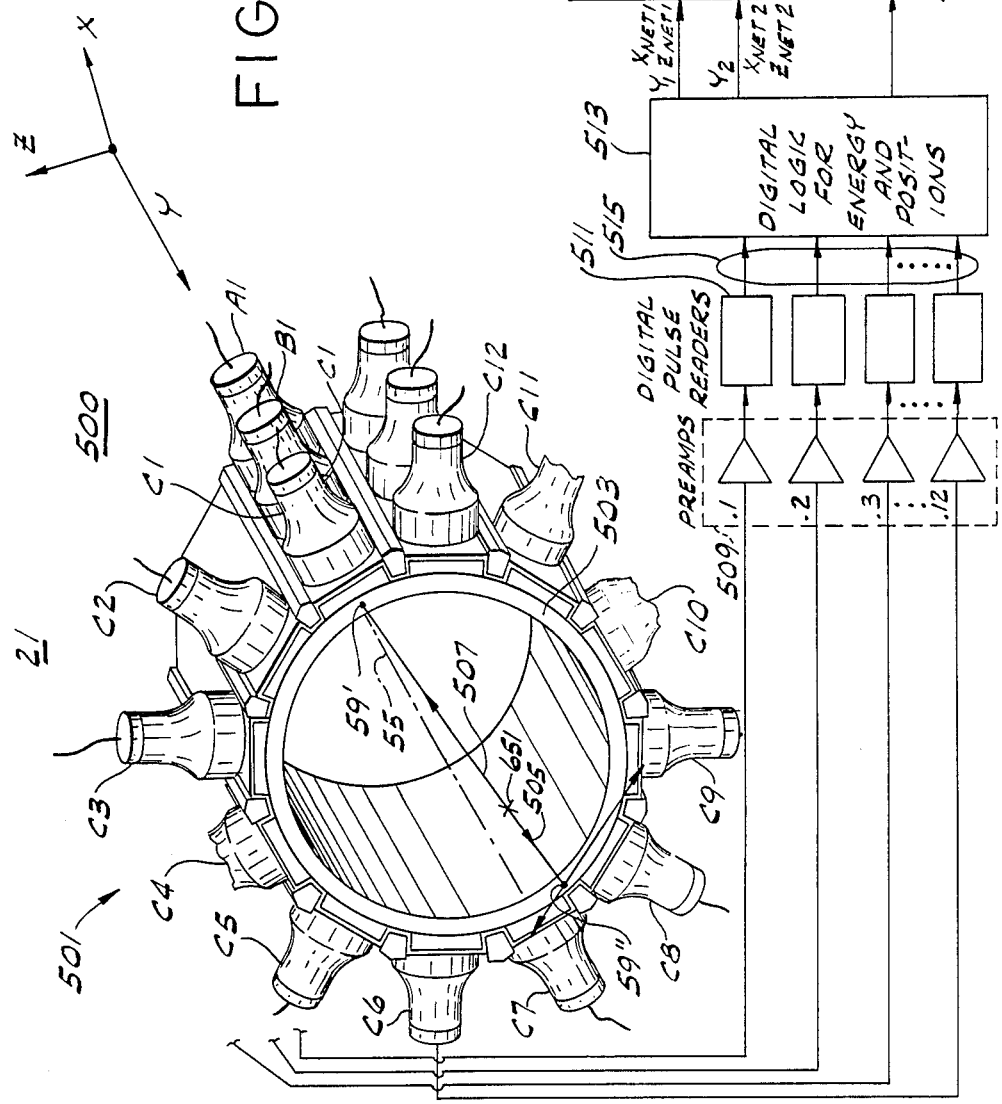

RADIATION IMAGING APPARATUS AND METHODS

Notice

Copyright © 1988 The Curators of the University of Missouri. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention relates to radiation imaging apparatus and methods. More particularly the present invention relates to radiation imaging apparatus and methods for gamma rays, neutrons, and positron annihilation radiation involving a tubular scintillation body with scintillation sensing units disposed along and around it.

A known type of photon imaging camera is known as the "Anger Scintillation Camera" as described for instance in *Nuclear Medicine Physics, Instrumentation, and Agents*, by F. D. Rollo, ed., C. V. Mosby Co., St. Louis, 1977, Chapter 6. The Anger scintillation camera employs a planar scintillation crystal with a two dimensional array of photomultiplier tubes (PMTs) arranged thereon. This camera permits a relatively accurate detection of photon event position, but has the crystal and the PMTs moved relative to the specimen in order to produce tomographic images, and images from a variety of directions for other imaging purposes. Moving the delicate apparatus in use is believed to present practical and economic difficulties. This camera receives photons of ionizing radiation from only a limited area in one direction at a time, so it has a relatively low volume imaging efficiency.

Another known type of photon imaging computer tomography apparatus is known as the "HEADTOME II", as described for instance in "A Hybrid Emission CT—HEADTOME II", by Y. Hirose et al., *IEEE Transactions on Nuclear Science*, Vol. NS-29, No. 1, February, 1982, pp. 520–523. The HEADTOME II as described therein utilizes three detector rings and collimators. Each ring contains 64 rectangular crystals each encapsulated in an aluminum housing and coupled directly to 64 photomultiplers respectively. The detector rings, which include the crystals and photomultipliers, wobble and rotate to achieve a minimum sampling spatial interval for positron study. A rotating collimator is used, and the detector rings also rotate for single photon studies. The rotation, and wobbling, motions are believed to result in practical and economic difficulties similar to those already mentioned in connection with the Anger scintillation camera, but in the HEADTOME II the motion is introduced to obtain accuracy in spatial resolution.

Adapting the known photon imaging devices for imaging of the whole human body increases the difficulties for at least mechanical and structural reasons due to the moving detector parts. The time required to scan the whole body is also increased. The cost of scaling up for whole-body imaging deters the use of known equipment which is already very costly at the smaller scale of imaging body parts.

SUMMARY OF THE INVENTION

Among the objects of the present invention are to provide radiation imaging apparatus in which the photomultiplier tubes or other sensors need not be moved either for reasons of complete specimen observation or adequate spatial resolution; to provide radiation imaging apparatus which has efficiency in volume imaging capability in the sense of detecting ionizing radiation emanating from many directions; to provide radiation imaging apparatus and methods which exhibit advantageous speed of sequential tomographic imaging; to provide radiation imaging apparatus and methods which enable simultaneous imaging in many tomographic planes; to provide radiation imaging apparatus and methods which simultaneously provide imaging in many tomographic planes which are contiguous as well; to provide radiation imaging apparatus and methods which can be used for tomographic and non-tomographic imaging of the whole human body or parts thereof; to provide radiation imaging apparatus which has a simple structure and is relatively economical to manufacture and use even for whole-body imaging; to provide radiation imaging apparatus and methods which are adapted to positron imaging, neutron imaging, and single photon imaging; to provide radiation imaging apparatus and methods which utilize or require relatively few photomultiplier tubes or other photosensitive devices and associated electronics; to provide radiation imaging apparatus and methods which simultaneously produce multiple two-dimensional images of the specimen; and to provide radiation imaging apparatus and methods which accomplish one or more of the foregoing objects with spatial resolution comparable to prior scintillation imaging apparatus.

Other objects and features will be in part apparent and in part pointed out hereinafter.

Generally, and in a first form of the invention, radiation imaging apparatus includes a substantially tubular body of material capable of producing scintillations in response to bombardment by ionizing radiation and means for converting the scintillations to electrical outputs including a plurality of scintillation sensing units disposed both along and around the outside of the substantially tubular body.

In general, another form of the invention involves radiation imaging apparatus for use with a substantially tubular body composed of a material capable of producing scintillations in response to bombardment by ionizing radiation, means for collimating the ionizing radiation having a substantially tubular structure positioned within the tubular scintillation body with a common axis and rotatable to different rotational positions, and means for converting the scintillations to electrical outputs, including a plurality of scintillation sensing units disposed both along and around the outside of the tubular scintillation body and having axial positions and positions relative to first and second coordinates perpendicular to the axis. The radiation imaging apparatus includes first means for computing in electrical form a weighted sum of the sums of the outputs of units having the same position relative to the first coordinate, and for computing in electrical form a weighted sum of the sums of the outputs of units having the same position relative to the second coordinate. The radiation imaging apparatus also includes second means for computing in electrical form a value of position for at least one of the scintillations as a function of the weighted sums for the first and second coordinates.

Generally, and in a method form of the invention, a radiation imaging method is used with a substantially tubular body composed of a material capable of producing scintillations in response to bombardment by ionizing radiation, means for collimating the ionizing radiation having a substantially tubular structure positioned within the tubular scintillation body with a common axis and rotatable to different rotational positions, and means for converting the scintillations to electrical outputs including a plurality of scintillation sensing units disposed both along and around the outside of the tubular scintillation body and having axial positions and positions relative to first and second coordinates perpendicular to the axis. The method includes the steps of computing in electrical form a weighted sum of the sums of the outputs of units having the same position relative to the first coordinate, computing in electrical form a weighted sum of the sums of the outputs of units having the same position relative to the second coordinate, and computing in electrical form an angular position for at least one of the scintillations as the arctangent of the ratio of the weighted sums for the first and second coordinates.

In general, and in yet another form of the invention, radiation imaging apparatus includes a substantially tubular scintillation body with a longitudinal axis, the body being composed of a material capable of producing photon events in response to bombardment by ionizing radiation, each photon event having a position relative to each of first and second coordinates perpendicular to the axis, and means for converting first and second photon events, resulting in said scintillation body from pairs of ionizing photons emitted by a positron annihilation event, to electrical outputs. The converting means includes rows of scintillation sensing units disposed around the outside of the tubular scintillation body. Means are also provided for generating for each row a sum of the outputs of the units therein, for identifying the row having the largest sum and the row having the second largest sum, for generating a value for the first coordinate position and a value for the second coordinate position of the first photon event from the sum for the row with the largest sum and the sums for at least its two adjacent rows, and for generating a value for the first coordinate position and a value for the second coordinate position of the second photon event from the sum for the row with the second largest sum and the sums for at least its two adjacent rows.

Generally, and in still another method form of the invention, a radiation imaging method is used with a substantially tubular scintillation body with a longitudinal axis, the body being composed of a material capable of producing photon events in response to bombardment by ionizing radiation, each photon event having a position relative to each of first and second coordinates perpendicular to the axis, and means for converting first and second photon events, resulting in the scintillation body from pairs of ionizing photons emitted by a positron annihilation event, to electrical outputs, the converting means including rows of scintillation sensing units disposed around the outside of the tubular scintillation body. The method includes the steps of generating for each row a sum of the outputs of the units therein and identifying the row having the largest sum and the row having the second largest sum. A value for the first coordinate position and a value for the second coordinate position of the first photon event are generated from the sum for the row with the largest sum and the sums for at least its two adjacent rows. Also, a value for the first coordinate position and a value for the second coordinate position of the second photon event are generated from the sum for the row with the second largest sum and the sums for at least its two adjacent rows.

In general, and in a further method form of the invention, a radiation imaging method is used with a substantially tubular body composed of a material capable of producing scintillations in response to bombardment by ionizing radiation, means for collimating the ionizing radiation having a substantially tubular structure positioned within the tubular scintillation body with a common axis and rotatable to different rotational positions, and means for converting the scintillations to electrical outputs including a plurality of scintillation sensing units disposed both along and around the outside of the tubular scintillation body and having axial positions and positions relative to first and second coordinates perpendicular to the axis. The method includes the steps of computing in electrical form a first weighted sum of the outputs of units, the output of each unit being weighted in the sum depending on its position relative to the first coordinate, and computing in electrical form a second weighted sum of the outputs of the units, the output of each unit being weighted in the second sum depending on its position relative to the second coordinate. The method further includes the step of computing in electrical form a value of position for at least one of the scintillations as a function of the first and second weighted sums for the first and second coordinates.

BRIEF DESCRIPTION OF THE DRAWINGS

FIG. 15 is a partially pictorial and partially block diagrammatic representation of positron annihilation radiation of the present invention;

Corresponding reference characters indicate corresponding parts throughout the several views of the drawings.

DETAILED DESCRIPTION OF PREFERRED EMBODIMENTS

Figure 1:
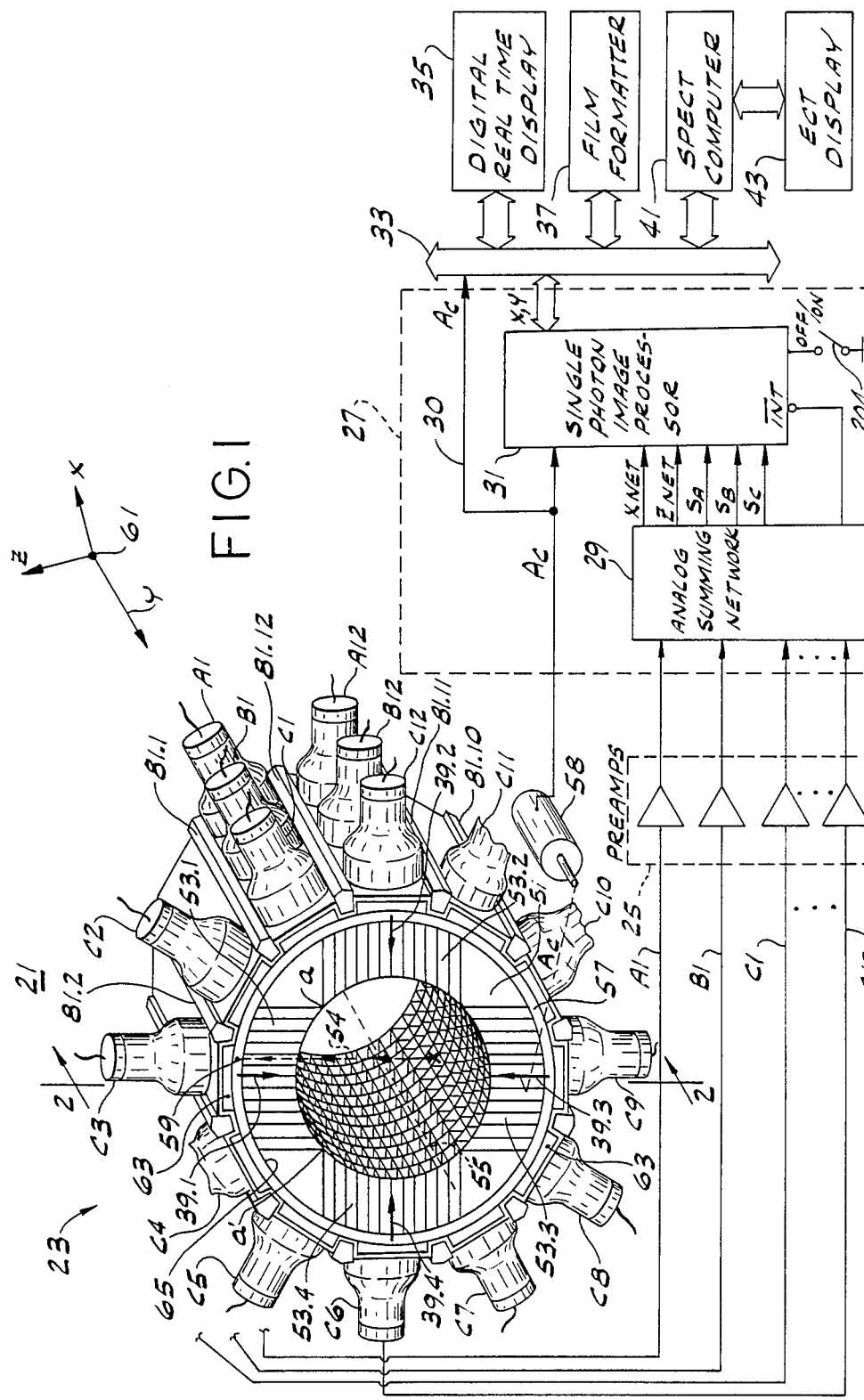
FIG. 1 is a partially pictorial and partially block diagrammatic representation of an embodiment of radiation imaging apparatus of the present invention.

In FIG. 1 a first form of radiation imaging apparatus of the invention is shown as a photon imaging apparatus 21 which includes a detector-collimator assembly 23, preamplifier array 25, and processing electronics 27 having an analog summing network 29, an encoder bus 30, and a block designated as a single photon image processor 31. Photon imaging apparatus 21 is coupled to a bus 33 and communicates to a digital real time display 35 and film formatter 37 for showing non-tomographic images as viewed along four mutually perpendicular collimator directions 39.1, 39.2, 39.3, and 39.4. The photon imaging apparatus 21 also communicates on bus 33 to a Single Photon Emission Computed Tomography (SPECT) computer 41, to which is attached an Emission Computed Tomography (ECT) display unit 43. SPECT computer 41 and ECT display unit 43 are readily available equipment, such as the ADAC Laboratories System 3300 SPECT computer system from ADAC Laboratories, Sunnyvale, Calif. Digital real time display apparatus 35 is composed of commercially available products such as a Gamma 11/23 computer from Digital Equipment Corporation, Boston, Mass., outfitted with digital display output circuits Model IP 512 and Model AP 512 from Imaging Technology, Inc., Woburn, Mass., to a video monitor such as Model SNA 15 from Conrac Corporation, Covina, Calif. Film formatter 37 is also a commercially available item such as the Matrix Video Imager, Model $M^2$, from Matrix Instruments, Inc., Northvale, N.J.

In detector-collimator assembly 23, a collimator 51 constitutes means for collimating ionizing radiation having a substantially tubular structure including four sections of lead (Pb) septa 53.1, 53.2, 53.3, and 53.4 defining channels of sufficient narrowness and depth to restrict passage of ionizing radiation, such as a gamma ray 54, to essentially the direction of the channels. One example of technology for manufacturing a collimator is discussed, for instance, in U.S. Pat. No. 4,181,839. The collimator 51 has a longitudinal axis 55 and is adapted to provide the four mutually perpendicular or orthogonal directions 39.1, 39.2, 39.3, and 39.4 of collimation, each of the four directions being perpendicular to the axis 55. Thus the collimator 51 tubular structure has four groups of substantially parallel generally transverse channels for quadriplanar collimation constituted by sections of septa 53.1, 53.2, 53.3, and 53.4 disposed both axially and circumferentially over at least a portion of the tubular structure for ionizing radiation to pass outwardly through the channels of the tubular structure into a tubular scintillation body 57. Collimator 51 is rotatable around the longitudinal axis 55 and has an angular position designated $A_c$ which is measured by a motor shaft encoder 58 that in turn feeds $A_c$ in binary coded decimal form (BCD) to single photon image processor 31 and bus 30. The encoder outputs, being digital in nature, can be directly input to latches for processor 31 and bus 33. Encoder 58 thus constitutes means for supplying information indicative of the rotational position of the collimator 51. Processing electronics 27 constitutes means for processing the electrical outputs from the PMTs and the rotational position information from encoder 58 to produce imaging information for a specimen within collimator 51 in electrical form.

Scintillation crystal 57 is a substantially tubular body of a material such as crystalline sodium iodide (NaI) or bismuth germanate ($Bi_4Ge_3O_{12}$) having a substantially tubular body concentrically surrounding collimator 51 and having axis 55 as a common central axis. In an example of manufacture, a 15 inch diameter, 7 inch long, solid cylindrical sodium iodide ingot is pulled from a melt. A hole is drilled parallel to the axis, followed by sawing out the inside of the tubular body with a band saw. The inner mass or plug of the ingot is removed, and the tubular body 57 remains. The inside surface as machined on a lathe to the inside diameter. The outer surface is machined to the outside diameter. The inner and outer surfaces are polished to optical quality. The removed plug is used in manufacturing other products for maximum economy. Harshaw Chemical Company of Cleveland, Ohio, is a source of such tubular scintillation bodies.

A patient is administered a radiopharmaceutical drug typically labelled with technetium-99m such as technetium-labelled dimethyl-triethyl-penta-acetic acid (DTPA) which emits gamma rays at an energy level of 140 kilo-electron-volts (KeV). Another example of a radio-pharmaceutical contemplated for use with the invention is a Tc-99m- labeled neutral lipophilic chelate such as Tc-99m-propyleneamine oxime (PnAO) which passively diffuses across the intact blood-brain barrier and rapidly clears from brain tissue. The patient or a body part of the patient constitutes a specimen (see FIG. 2) which is placed along axis 55 within the collimator 51 and emits ionizing radiation. The ionizing radiation bombards and inelastically collides with the crystalline material of the scintillation body 57 producing a scintillation, or photon event, 59. Photon event 59 consists of a shower of non-ionizing photons (such as visible photons) in all directions. Sodium iodide, for example, has a rolloff or half-time on the order of one fourth of a microsecond, and as many as 500,000 counts per second are contemplated. Scintillation body 57 thus constitutes a substantially tubular body of material capable of producing scintillations in response to bombardment by ionizing radiation. Collimator 51 is positioned within tubular body 57 substantially coaxial therewith.

By virtue of the tubular, continuous, nonsegmented, and nonseparated construction of the scintillation body 57, the photons emanating from the photon event 59 reach in varying proportions at least some of 36 photomultiplier tubes (PMTs) A1, B1, C1, A2, B2, C2, A3, B3, C3, A4, B4, C4, A5, B5, C5, A6, B6, C6, A7, B7, C7, A8, B8, C8, A9, B9, C9, A10, B10, C10, A11, B11, C11, and A12, B12, and C12. (Some of the PMTs are not shown in FIG. 1 for clarity.) The whole scintillation body 57 constitutes a single optical entity for the PMTs, in contrast to separate detector crystals for the PMTs respectively. An X-Y-Z rectangular coordinate system 61 having its Y axis coincident with axis 55 is shown in a deliberately predetermined orientation relative to detectorcollimator assembly 23 and is discussed in greater detail hereinafter. The array 25 of 36 preamplifiers is connected respectively to the 36 PMTs. Not shown is a high voltage power supply for the PMTs, and details of the circuitry of the preamplifiers 25, which are well known to those skilled in the art. A description of such features is found in the above-cited *Nuclear Medicine Physics, Instrumentation, and Agents*.

Scintillation body 57 is an extended annulus having an axis and composed of a substance capable of scintillating in flashes in response to particles of ionizing radiation. The PMTs constitute means for converting the scintillations to electrical impulses or outputs and include a plurality of units disposed both along and around the outside of the body 57. The PMTs constitute units in means for converting the scintillations which in sodium iodide are at visible wavelengths, to electrical outputs (on lines marked to correspond to PMTs A1, B1, C1, A2, B2, C2, . . . A12, B12, C12), including a plurality of units disposed both axially and circumferentially around the outside of the body of the scintillation body 57 on a concentric intermediate Pyrex glass window 63 illustratively sectioned into twelve segments or faces. The window 63 is consequently capable of inexpensive manufacture in identical pieces. The glass window 63 constitutes light transmissive means having substantially planar exterior faces and surrounding the tubular scintillation body 57, each unit, or PMT, of the converting means being urged against one of the planar exterior faces of the light transmissive means. Light-coupling grease is applied between the PMT, and the window 63. The segments of window 63 are fitted snugly to tubular body 57.

A thin tubular sleeve or element 65 of aluminum is inserted in scintillation crystal 57 and covers the inside surface thereof. The tubular sleeve 65 is substantially transparent to ionizing radiation and substantially opaque to light of wavelengths of scintillations produced by scintillation body 57, and surrounds the collimator 51 and is thus located between the collimator 51 and the scintillation body 57.

Preamplifiers 25 produce analog electrical impulses, having a height which is proportional to the number of visible photons impinging on each of the PMTs A1-C12 from photon event 59, and send them to the analog summing network 29.

Advantageously the PMTs, or converting means, are substantially fixed, and the collimator 51 is rotatable relative to the PMTs. The embodiment of FIG. 1 obviates the engineering and economic complications of rotating, moving, wobbling, or nutating of these relatively delicate parts.

The PMTs are arranged in exactly twelve groups or rows of three axially disposed units each in the embodiment of FIG. 1. The units in the rows are physically aligned in that they have respective axial positions and the axial positions of the units in each group or row are substantially the same as the respective axial positions of the units in the other groups. In other embodiments it is believed to be preferable that the PMTs be arranged in at least eight groups of at least two axially disposed units each, the at least eight groups of units being circumferentially disposed around the body of the scintillation crystal 57 for high volume imaging efficiency and imaging from many directions and to generate data from a sufficient number of directions to obtain a well-defined tomographic image from ECT display 43. In other embodiments the PMTs can be replaced by other scintillation sensing units.

It is to be understood that although the apparatus of FIG. 1 is described in connection with an example of imaging photons, such as gamma rays, of ionizing radiation, the same apparatus is contemplated for use for imaging a source of neutrons or other particles. In the case of neutrons, a radiopharmaceutical labelled with an isotope such as californium-252 is used as a source, and either sodium iodide (NaI) or another suitable scintillation material is used for tubular body 57.

Figure 2:
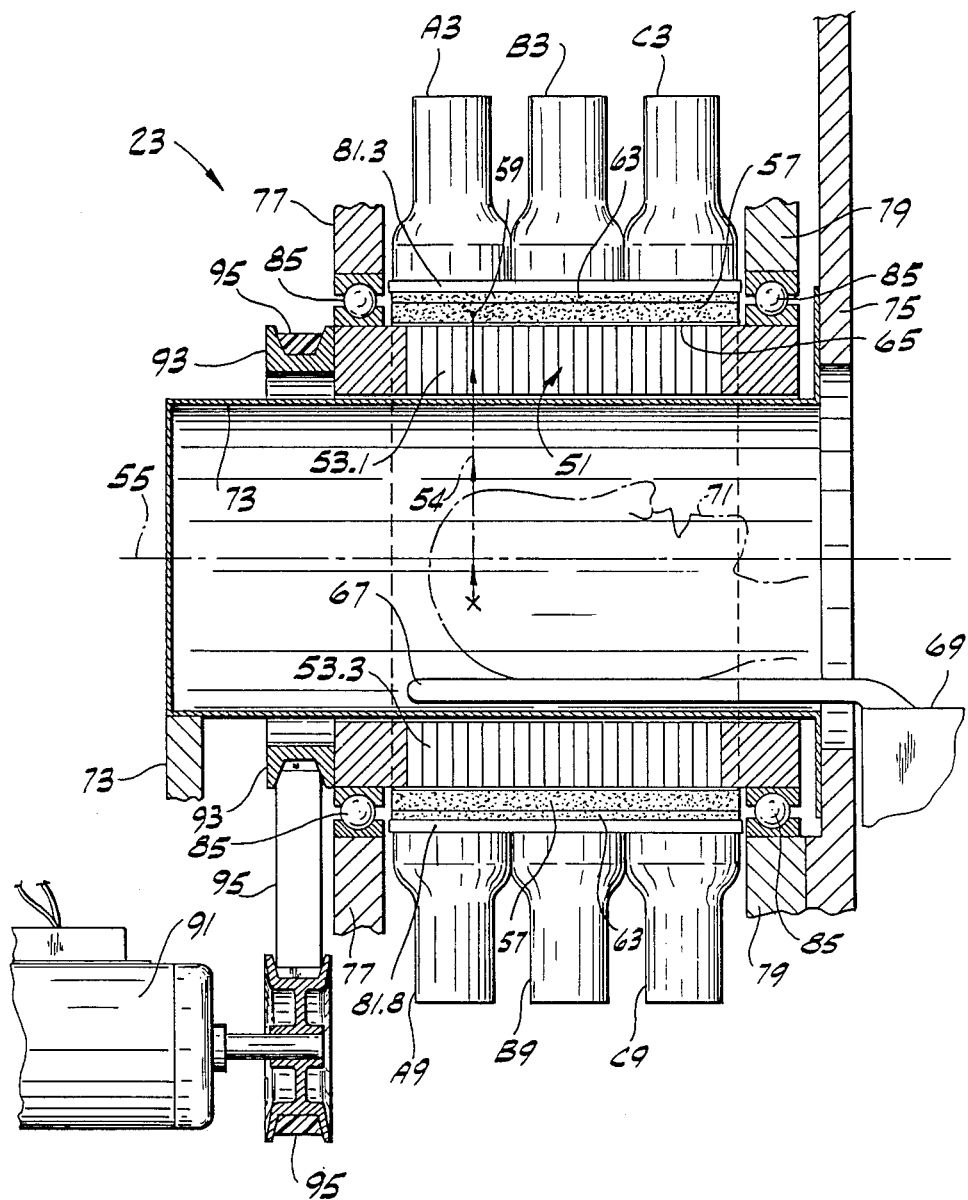
FIG. 2 is a cross-section of a detector-collimator assembly of the invention shown pictorially in FIG. 1, showing a drive mechanism and additional mechanical support structure.

FIG. 2 shows a vertical cross-section through the detector-collimator assembly 23 along line 2—2 of FIG. 1. Collimator sections 53.1 and 53.3 as well as tubular aluminum sleeve 65, scintillation body 57 are seen in their longitudinal aspect. The window 63 with top PMTs A3, B3, and C3 and bottom PMTs A9, B9, and C9 flank the scintillation crystal 57. A head rest 67 of a patient table 69 support a patient's head 71 within collimator 51. A stationary aluminum protective liner 73 which is transparent to ionizing radiation fills the inside of collimator 51 and is in turn supported by support structure 73 and gantry 75. The liner 73 is opaque so that rotation of collimator 51 is not visible to the patient. The PMTs, window 63, tubular body 57 and sleeve 65 are firmly attached to and supported by fixed support members including apertured end plates 77 and 79. The window 63 is made of twelve sections of Pyrex (trademark) glass which constitute the faces thereof. The PMTs have lateral brackets or skirts (not shown), which with the glass faces of window 63 are held together against the crystal 57 by twelve longitudinal hold-down strips 81.1, 81.2, . . . , 81.12. Hold-down strips 81.3 and 81.8 are shown in FIG. 2. The hold-down strips are affixed to the aluminum end plates 77 and 79. Collimator 51 is rotatably mounted to the end plates 77 and 79 by bearings 85. Motor 91, to the shaft of which encoder 58 of FIG. 1 is attached, drives a toothed pulley 93 which is affixed to the collimator 51.

Toothed timing belt 95 couples motor 91 to toothed pulley 93. A light-tight shield (not shown) for each PMT is affixed to each PMT bracket. The whole assembly is covered with a removable fiberglass shield (not shown) for aesthetics and dust protection.

Figure 3:
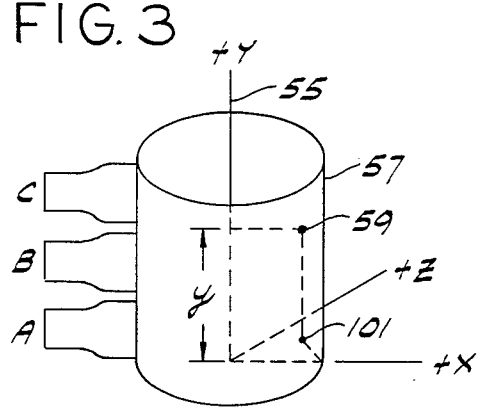
FIG. 3 shows a coordinate system relative to a simplified sketch of the detector-collimator assembly for analyzing the operations of the present invention.

FIG. 3 shows a simplified sketch of the tubular crystal 57 with three of the PMTs generally indicated by the letters A, B, and C. Coordinate axes X, Y, and Z are indicated for comparison with the same axes shown in FIG. 1. Scintillation 59 in tubular body 57 is projected to the Y axis and has an axial position y. Scintillation 59 in crystal 57 is also projected to the X-Z plane at point 101.

Figure 4:
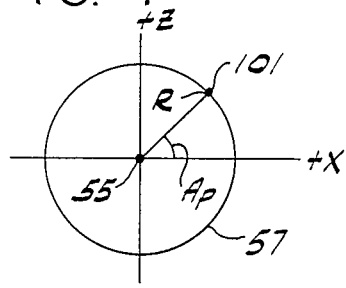
FIG. 4 shows an X-Z coordinate plane for defining an angle $A_p$.

FIG. 4 shows point 101 in the fixed X-Z plane. Tubular body 57 intersects the X-Z plane in a circle or ring in FIG. 4. Point 101 has an angular position $A_p$ relative to the +X axis in the X-Z coordinate system and is located a distance R from axis 55.

Figure 5:
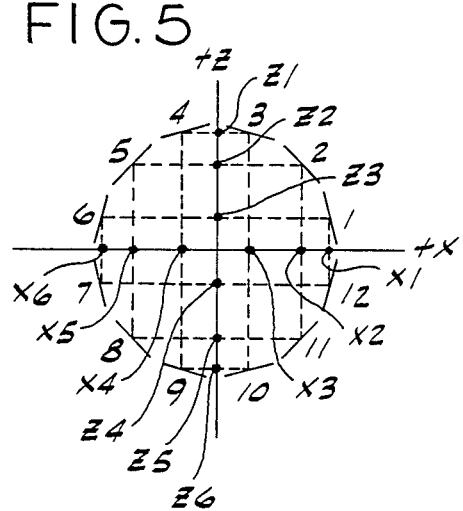
FIG. 5 shows the position and numbering of photomultiplier tubes around the Y axis in the X-Z plane.

FIG. 5 defines the position of the X-Z coordinate system by showing the X axis bisecting the window 63 into symmetric halves at vertices between faces 1,12 and faces 6,7. The Z axis is normal to the X axis. The faces of window 63, and thus rows of PMTs having the same angular or circumferential position, are herein assigned numbers 1–12 relative to the stationary X-Z coordinates as shown in FIG. 5. Thus, PMTs A1, B1, C1 are located at face 1 of FIG. 5, for example. In FIG. 3, the general positions A, B, and C indicate axial positions of the PMTs, so that for example, all of PMTs B1, B2, ... B12 are at the axial position B.

Figure 6:
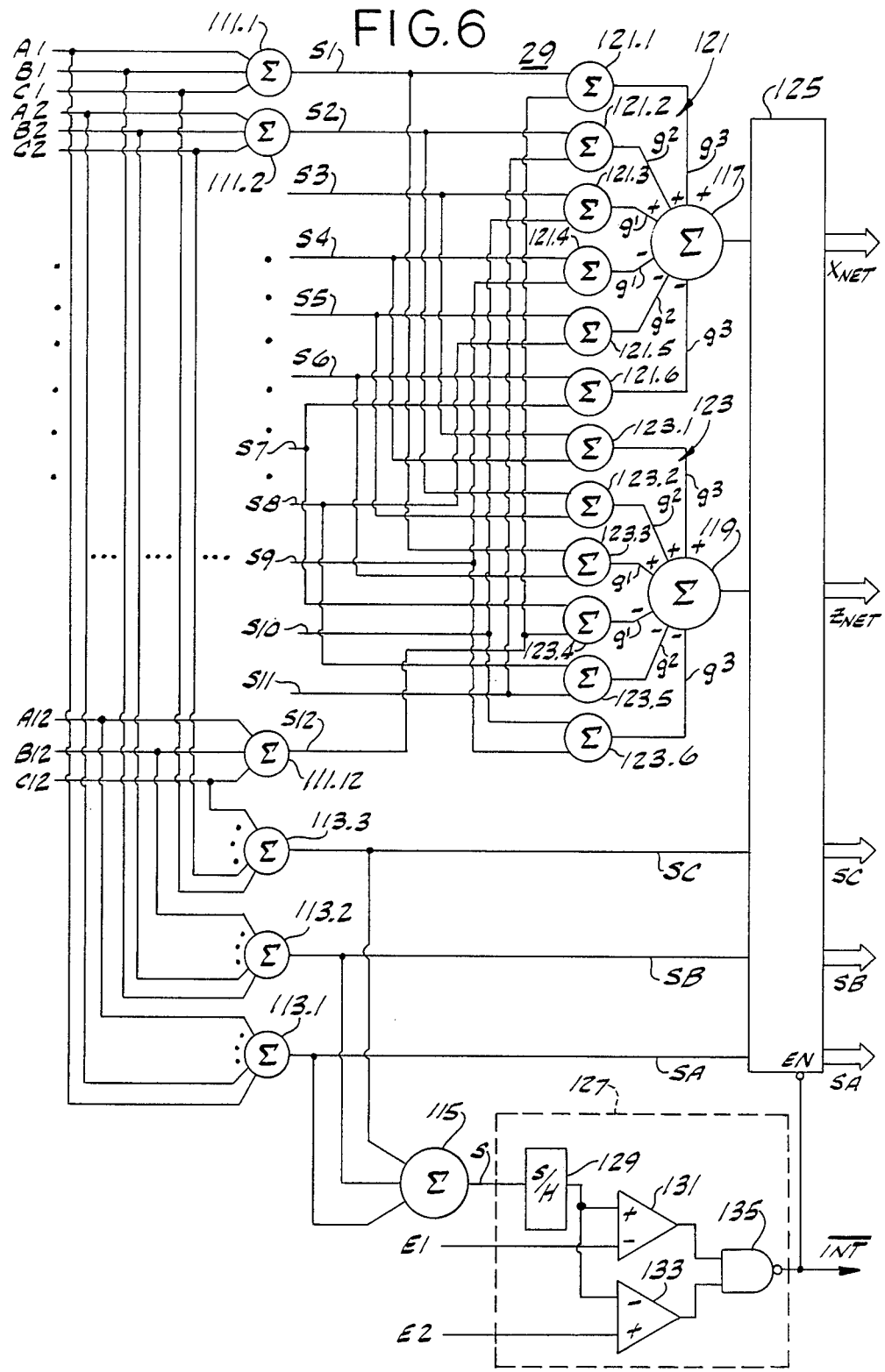
FIG. 6 is a schematic diagram of an analog summing network for the apparatus of FIG. 1.

In FIG. 6, a schematic diagram of analog summing network 29 of FIG. 1 is shown. Analog summing network 29 receives PMT outputs as amplified by preamplifiers 25 of FIG. 1. These outputs are designated A1, B1, C1, A2, B2, C2, ..., A12, B12, C12 in FIG. 6 to correspond with all 36 PMT outputs. The outputs from each row as numbered in FIG. 5 are summed by 12 three-input summers 111.1, 111.2, ..., 111.12 to respectively produce twelve outputs S1, S2, ..., S12 according to the following formulas:

$$S1 = A1 + B1 + C1 \tag{1}$$

$$S2 = A2 + B2 + C2 \tag{2}$$

$$S3 = A3 + B3 + C3 \tag{3}$$

$$S4 = A4 + B4 + C4 \tag{4}$$

$$S5 = A5 + B5 + C5 \tag{5}$$

$$S6 = A6 + B6 + C6 \tag{6}$$

$$S7 = A7 + B7 + C7 \tag{7}$$

$$S8 = A8 + B8 + C8 \tag{8}$$

$$S9 = A9 + B9 + C9 \tag{9}$$

$$S10 = A10 + B10 + C10 \tag{10}$$

$$S11 = A11 + B11 + C11 \tag{11}$$

$$S12 = A12 + B12 + C12 \tag{12}$$

Three 12-input analog summers 113.1, 113.2, and 113.3 compute three "axial sums" SA, SB, and SC of the outputs of PMTs having the same axial position according to the following three formulas:

$$SA = A1 + A2 + A3 + A4 + A5 + A6 + A7 + A8 + A9 + A10 + A11 + A12 \tag{13}$$

$$SB = B1 + B2 + B3 + B4 + B5 + B6 + B7 + B8 + B9 + B10 + B11 + B12 \tag{14}$$

$$SC = C1 + C2 + C3 + C4 + C5 + C6 + C7 + C8 + C9 + C10 + C11 + C12 \tag{15}$$

A three-input analog summer 115 is connected to the outputs of summers 113.1, 113.2, and 113.3 and computes a sum S indicative of the total number of photons received at the PMTs from photon event 59, and indicative of the energy deposited in the scintillation body 57 by photon event 59. The sum S is calculated according to the formula:

$$S = SA + SB + SC \tag{16}$$

A pair of six-input analog summers 117 and 119 each have three plus inputs and three minus inputs. (All other summers in FIG. 6 which have no sign marked next to their inputs have all plus inputs.) Summer 117 is fed from a set of six analog summers 121.1, 121.2, 121.3, 121.4, 121.5, and 121.6. Summer 119 is fed from another set of six analog summers 123.1, 123.2, 123.3, 123.4, 123.5, and 123.6. Each of the analog summers in the sets numbered 121 or 123 produces an output proportional to the sum of six outputs of PMTs all having the same position relative to the X or Z coordinate in FIG. 5. For instance in FIG. 5, the six PMTs A1, B1, C1, A12, B12, C12 all have the same X coordinate position X1. Similarly, all six PMTs on faces 2,11 and 3,10 have the same positive X coordinate position X2 and X3 respectively. The sets of six PMTs on faces 4,9; 5,8; and 6,7 have the same negative X coordinate position X4, X5, and X6 respectively.

The six PMTs A3, B3, C3 and A4, B4, C4 all have the same Z coordinate position Z1. Similarly, all six PMTs on faces 2,5 and 1,6 have the same positive Z coordinate position Z2 and Z3 respectively. The sets of six PMTs on faces 7,12; 8,11; and 9,10 have the same negative Z coordinate position Z4, Z5, and Z6 respectively.

Accordingly, in FIG. 6 summers 121.1–121.6 have their twelve inputs (2 inputs for each of the six summers) connected to summers 111.1–111.12 so that the six outputs of summers 121.1–121.6 are the sums for the six respective sets of six PMTs having the same X coordinate position X1, X2, X3, X4, X5, X6. Summer 117 with summers 121.1–121.6 constitutes means for computing a position $X_{net}$ for the photon event 59 relative to coordinate X as a weighted sum of the sums of the outputs of units having the same position relative to coordinate X.

The summers 123.1–123.6 have their twelve inputs (2 inputs for each of the six summers) connected to summers 111.1–111.12 so that the six outputs of summers 123.1–123.6 are the sums for the six respective sets of six PMTs having the same Z coordinate position Z1, Z2, Z3, Z4, Z5, Z6. Summer 119 with summers 123.1–123.6 constitutes means for computing a position $Z_{net}$ for the photon event 59 relative to coordinate Z as a weighted sum of the sums of the outputs of units having the same position relative to coordinate Z.

"Weighted sum" as the phrase as used herein denotes addition of any set of numbers including negative numbers as well as positive numbers and with positive or negative coefficients. A linear combination is a weighted sum. Negative inputs of the analog summers 117 and 119 are indicated by a minus sign, and are used for reversing the polarity of the analog outputs of the summers which sum respective sets of six PMT outputs on negative X and negative Z positions. These summers are summers 121.4, 121.5, 121.6 and the summers 123.4, 123.5, and 123.6. The sums of sets of six PMT outputs from the summers 121.1–121.6 are weighted by analog means such as adjustable voltage dividers or gain-adjusting potentiometers so as to apply weights $g_1$, $g_2$, and $g_3$ as marked next to the six inputs of summer 117 and the six inputs of summer 119. The values of weights are derived by the skilled worker as discussed in the section entitled "Computation of g and k Constants" hereinbelow.

The positions $X_{net}$ and $Z_{net}$ are computed by the analog summing network 29 of FIG. 6 according to the formulas:

$$X_{net} = g_1(S3+S10) + g_2(S2+S11) + g_3(S1+S12) \\ - [g_1(S4+S9) + g_2(S5+S8) + g_3(S6+S7)] \quad (17)$$

$$Z_{net} = g_1(S6+S1) + g_2(S5+S2) + g_3(S4+S3) \\ - [g_1(S7+S12) + g_2(S8+S11) + g_3(S9+S10)] \quad (18)$$

The analog summing network 29 is also regarded as computing a position for the photon event 59 relative to the first coordinate X by computing the weighted sum as the difference of a first weighted sum of the sums of the outputs of units having the same positive value of the first coordinate position and a second weighted sum of the sums of the outputs of units having the same negative value of the first coordinate position; and computing the position for the photon event 59 relative to the second coordinate Z by computing the weighted sum as the difference between a first weighted sum of the sums of the outputs of units having the same positive value of the second coordinate position and a second weighted sum of the sums of the outputs of units having the same negative value of the second coordinate position.

An analog-to-digital converter (ADC) 125 with sample and hold provides digital representations of axial sums SA, SB, and SC and of positions $X_{net}$ and $Z_{net}$. It is desirable, however, to avoid providing such digital representations at the output (to the right of the ADC 125) if the photon event 59 being measured lies outside of predetermined energy range values E1 and E2 that indicate a valid or expected type of ionizing photon event. Accordingly, a circuit 127 is provided for enabling ADC 125 at pin EN and interrupting processor 31 of FIG. 1 only when sum S is greater than energy value E1 and less than energy value E2. Circuit 127 is known as a single channel analyzer circuit in the art, and it is to be understood that S, E1, and E2 are scaled by the skilled worker to accomplish selection in the energy range with normal circuit voltage levels. Circuit 127 is illustratively implemented by sample and hold circuit 129 for sampling and holding the sum S output of summer 115 and by comparators 131 and 133 feeding NAND gate 135. The output INT-bar of NAND-gate 135 only goes active-low when the outputs of comparators 131 and 133 are both high. The comparator outputs are both high only when sum S as sampled by circuit 129 exceeds energy value E1 and is exceeded by energy value E2. When technetium-99m is the gamma source, energy values E1 and E2 are set nominally 125 KeV and 155 KeV, respectively, to bracket the 140 KeV expected gamma rays by plus and minus 10%.

Figure 7:
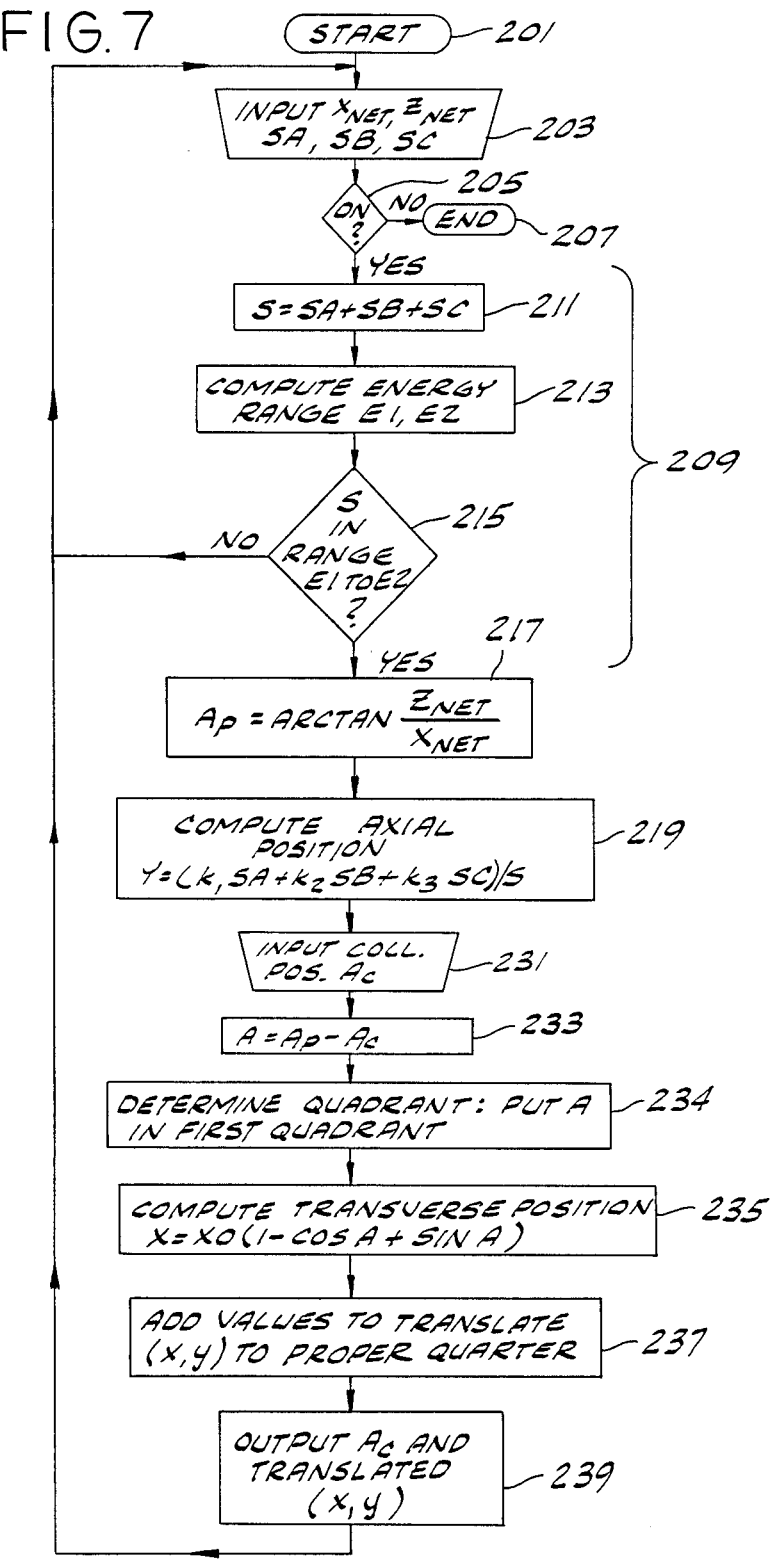
FIG. 7 is a flowchart of operations of a single photon image processor for FIG. 1 according to a method of the invention.

FIG. 7 illustrates a flow of operations for single photon image processor 31, which is implemented with an inexpensive microcomputer, when used with analog summing network 29 of FIG. 1. The microcomputer can either be dedicated or be the computer in the digital real time display apparatus 35 or be otherwise provided. Operations commence at start 201 and input at step 203 the digital representations for $X_{net}$, $Z_{net}$, SA, SB, and SC from analog summing network 29 as soon as they are made available by interrupt output INT-bar. At step 205, the processor 31 checks an Off/On switch 204 to determine if the system is on or off, and if off then end 207 is reached.

At steps 209, a test for a valid photon event 59 is made. Sum S is computed digitally from axial sums SA, SB, and SC in step 211. Energy range values E1 and E2 are either recalled from store or calculated in step 213 for designating the range of energies that indicate a valid ionizing photon event 59. If sum S is in the range E1 to E2, operations proceed to step 217, otherwise they branch back to step 203.

At step 217, a computed angle $A_p$ for the point 101 in the X-Z plane as shown in FIG. 4, is obtained according to the formula:

$$A_p = \text{Arctan}(Z_{net}/X_{net}) \quad (19)$$

In this way the processor 31 also computes an angular position $A_p$ for at least one of the scintillations substantially as the arctangent of the ratio of the weighted sums for the X and Z coordinates. Since either or both of the weighted sums $Z_{net}$ and $X_{net}$ can be negative as well as positive, the arctangent function in processor 31 written to be able to yield values of $A_p$ from zero through 360°.

At step 219, an axial position y of the photon event is calculated according to the formula:

$$y = (k_1 SA + k_2 SB + k_3 SC)/S \quad (20)$$

Equation (20) involves three constants $k_1$, $k_2$, and $k_3$ for the detector-collimator assembly 23 which are determined in the manner described in the section entitled "Computation of g and k Constants" hereinbelow.

Together with the axial position y, the angular position $A_p$ conveys position information for photon event 59. For many imaging and tomography purposes it is also helpful to further calculate a value herein called the transverse position x from the angular position $A_p$. The transverse position of the photon event 59 is its position on a transverse dimension in a conceptual viewing plane which travels with the collimator 51.

Figure 8:
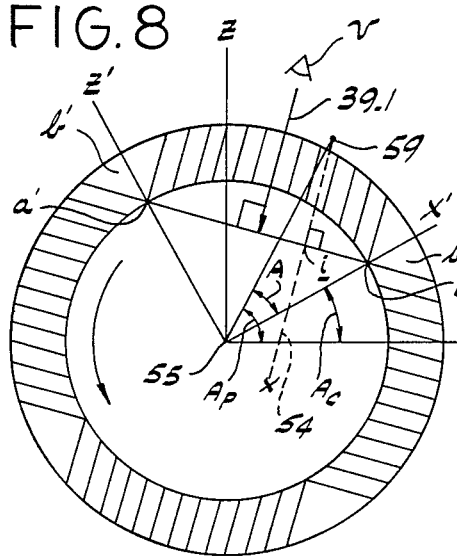
FIG. 8 is a diagram of a rotating "primed" coordinate system $X'-Z'$ attached to the collimator of FIG. 1 shown relative to the X-Z plane for defining an angle $A_c$ and a viewing plane.

In FIG. 8, the viewing plane extends into the paper parallel to axis 55 and is seen on edge as a line a–a' between vertices a and a' of blind zones b and b' of collimator 51. The line a–a' defines the transverse dimension. A set of coordinate axes X' and Z' pass through the vertices a and a'. The coordinate axes X' and Z' are rotating coordinates which are associated with the collimator 51 and move relative to the stationary coordinates X and Z, making the collimator angle $A_c$. Photon event 59 has angular position $A_p$ in FIG. 8 just as in FIG. 4. The photon event 59 has an angle value A of position in the rotating X'-Z' coordinates which is the difference $A_p - A_c$. A conceptual viewer v peers along direction of collimation 39.1 normal to viewing plane a–a'. Because of the collimating action of collimator 51, only radiation 54 which is parallel to a direction of collimation such as direction 39.1 passes through the collimator and produces the photon event 59. Viewer v sees an image point i where radiation 54 intersects viewing plane a-a'.

Figure 9:
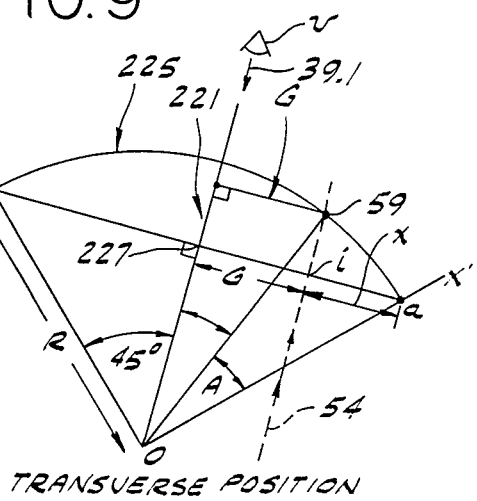
FIG. 9 is a geometric construction of the relationship between the position of a photon event or scintillation in the rotating $X'-Z'$ coordinate system of FIG. 8 and the transverse position of the photon event in a viewing plane normal to a direction of collimation.

FIG. 9 is like FIG. 8, except in being marked for more detailed discussion. For clarity the stationary X and Z coordinates and markings for angular position $A_p$ and collimator angle $A_c$ are omitted in FIG. 9. FIG. 9 is geometrically analyzed to obtain an equation for transverse position x which is used in the operations of FIG. 7 of single photon image processor 31.

In FIG. 9 an artificial construction line 221 is drawn in the direction of collimation 39.1 through the origin O (on axis 55) at a 45° angle to the rotating coordinate system X'-Z'. Next a segment G is drawn perpendicular to line 221 through photon event 59. Photon event or scintillation 59 is located on a circle 225 of radius R at angle A which is equal to $A_p - A_c$. R is the radial distance to the point P of photon events which is approximately equal to the 15.0 centimeter inside radius of the 12 millimeter thick scintillation body 57 plus an average penetration depth of 3.0 millimeters for sodium iodide at 140 KeV. A point 227 where line 221 intersects viewing plane a-a' is regarded as corresponding to a transverse position x of 0.5 times the radius R times the square root of 2, here indicated as 0.5SQRT(2)R. Point a has a transverse position of 0, and point a' has a transverse position of SQRT(2)R. In other words, when a photon event 59 occurs on the X' axis (i.e. $A_p = A_c$), then the transverse position x is zero. When the event 59 occurs on the Z' axis (i.e. $A_p = A_c + 90°$), then the transverse position x is SQRT(2)R.

In general, the transverse position of image point i for photon event 59 is given by the formula x=0.5SQRT(2)R−G where the length of segment G is Rsin(45°−A). With a little trigonometric manipulation the following equation is obtained:

$$x = 0.707R(1 - \cos A + \sin A) \text{ tm} \quad (21)$$

The foregoing discussion has assumed that the angle A lies between 0 and 90 degrees. When A lies outside this range, it is translated into the first quadrant according to the process discussed next.

Equation 21 is relatively efficient of computer time. Collimator angle $A_c$ is input from encoder 58 of FIG. 1 at step 231 of FIG. 7. The angle value A is obtained by computing the difference $A = A_p - A_c$ at step 233.

In step 234 of FIG. 7, the angle value A is tested to determine which quadrant (0°–90°, 90°–180°, 180°–270°, 270°–360°) includes angle value A. This is accomplished, for instance by repeatedly subtracting 90° from angle value A until the result is negative. The number of such subtractions is equal in number to the respective first, second, third, or fourth quadrant. Then 90° is added back to the negative result to put A in the first quadrant.

In step 235 transverse position x is calculated by computing the cosine and the sine of the angle value A resulting from steps 233 and 234. The sum of one minus the cosine plus the sine of angle A is computed and this sum is multiplied by any appropriate transverse position scaling factor X0 which the skilled worker may select in lieu of the factor 0.707R in Equation 21. The transverse position thus obtained completes step 235.

It is to be noted that in other methods or embodiments, other equations which appear quite different but accomplish similar results can be selected by the skilled worker. For example, by use of trigonometric identities Equation 21 is written equivalently as:

$$x = 0.707R[1 - (\cos A_c - \sin A_c)\cos A_p + (\cos A_c + \sin A_c)\sin A_p] \quad (21')$$

Still another equivalent equation is:

$$x = 0.707R[1 + SQRT(2)\sin(A - 45°)] \quad (21'')$$

Equation 21" requires one less trigonometric function computation by processor 31 and may be preferable in some embodiments. It is also apparent from equation 21" that transverse position as a function of angle value A is relatively linear in the region from zero to 90°, so that the skilled worker may also approximate the transverse position equation with a linear, cubic or higher polynomial approximation. The linear approximation is given as:

$$x = 0.707R[1 + 1.414(A - pi/8)] \quad (21''')$$

where pi is the number 3.1415926535 . . . . It is to be understood that all such approximations and other equivalent expressions are contemplated in the practice of the invention. The equation is calculated directly by appropriate computer calculating operations or by use of lookup tables of any given trigonometric or other function or by other procedures known to the skilled worker.

Steps 217, 233, 234 and 235 constitute computing in electrical form a value of position for at least one of the scintillations as a function of the first and second weighted sums $X_{net}$ and $Z_{net}$ for the first and second coordinates X and Z. Moreover, these steps constitute computing in electrical form a transverse position for at least one of the scintillations substantially proportional to the function $(1 - \cos A + \sin A)$ where A is the difference between the arctangent of the ratio of the first and second weighted sums and an angular position of the collimating means. In addition, these steps constitute computing in electrical form a transverse position for at least one of the scintillations as a function of the ratio of the weighted sums for the first and second coordinates X and Z.

Collimator 51 has four directions of collimation 39.1, 39.2, 39.3, and 39.4. A photon event 59 can occur at any angular position $A_p$ around the scintillation crystal 57. Accordingly, the processor 31 is made to operate to produce image data for each of four views of the specimen as seen respectively along the four directions of collimation. A single photon event such as event 59 contributes to one of the four views. Since many photon events occur, of which event 59 is but one example, image data for all four views of the specimen are built up over time. Readily available digital real time display apparatus 35 and film formatter equipment 37 of FIG. 1 are generally constructed to build up single images from image data consisting of pairs of coordinate values. Because processor 31 is producing image data for each of four views of the specimen, it is very desirable to produce pairs of x,y values which are of such a type that four views show up on the readily available display apparatus 35 and film formatter equipment 37. To accomplish this compatibility, processor 31 advantageously calculates values of transverse position x and axial position y to which a predetermined number for X0 (such as SQRT(2)R) has been added in accordance with step 237.

Figure 10:
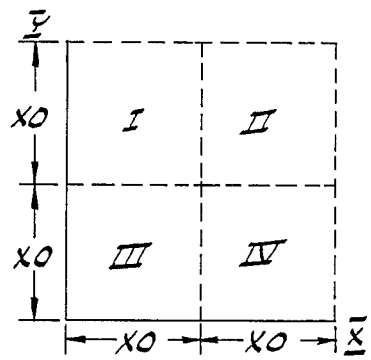
FIG. 10 is a diagram illustrating four quarters of a single composite display of four images in viewing planes normal to each of the four directions of collimation of the collimator of FIG. 1.

Assume that the x and y values have been scaled so that they fall in a square of dimensions X0 by X0, and that X0 is selected for an image field of 2X0 by 2X0 in the digital real time display 35 and the film formatter 37. As shown in FIG. 10, it is desired to translate the views into each of four quarters I, II, III, and IV in the image field. This is accomplished in step 237 by processor 31 by the following procedure: If A is in the 1st quadrant, then add X0 to y in the data pair (x,y) for the transverse and axial position; if A is in the 2nd quadrant, then add X0 to both x and y in (x,y); if A is in the 3rd quadrant, then do not change either x or y; and if A is in the 4th quadrant, then add X0 to x in (x,y).

Then in step 239 of FIG. 7 processor 31 outputs each pair (x,y) processed in accordance with step 237. The collimator angle $A_c$ is also made available either by processor 31 or as binary coded decimal position information directly on bus 30, as the skilled worker elects, to bus 33 for tomography and nontomographic imaging purposes.

Figure 11:
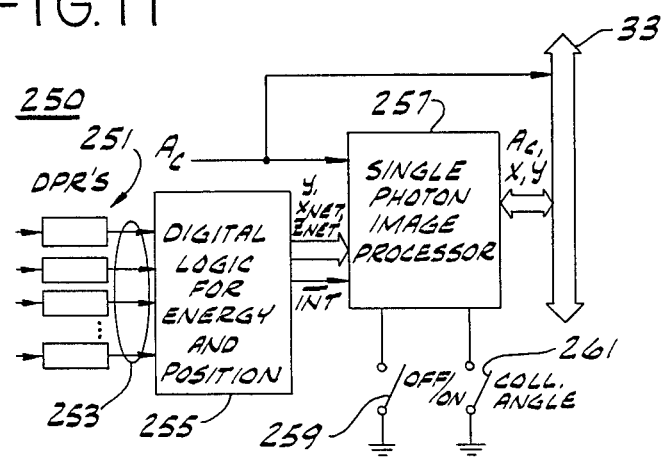
FIG. 11 is a block diagram of alternative processing electronics of the invention for use in the inventive apparatus of FIG. 1.

FIG. 11 shows an alternative all-digital embodiment for processing electronics 27 of FIG. 1. In FIG. 11, processing electronics 27 of FIG. 1 is replaced by all digital processing electronics 250. Digital pulse readers (DPRs) 251 convert the analog pulses from each of the preamplifiers 25 in FIG. 1 into digital representations having nominally 8 bits. These digital representations are sent on 36 8-bit buses 253 to digital logic 255, where the digital representations are temporarily stored in data registers or latches. Digital logic 255 includes a microcomputer for accomplishing digitally the operations performed by the analog summing network 29 of FIG. 1. A single photon image processor 257, which includes a microcomputer, receives information from digital logic 255 and computes an (x,y) pair of transverse and axial position values for each scintillation for bus 33. An On/Off switch 259 is provided for processor 257. A collimator angle mode switch 261 is set by user to select computations for continuously variable collimator angle $A_c$ or alternatively to select computations for a few preselected values of collimator angles $A_c$.

Figure 12:
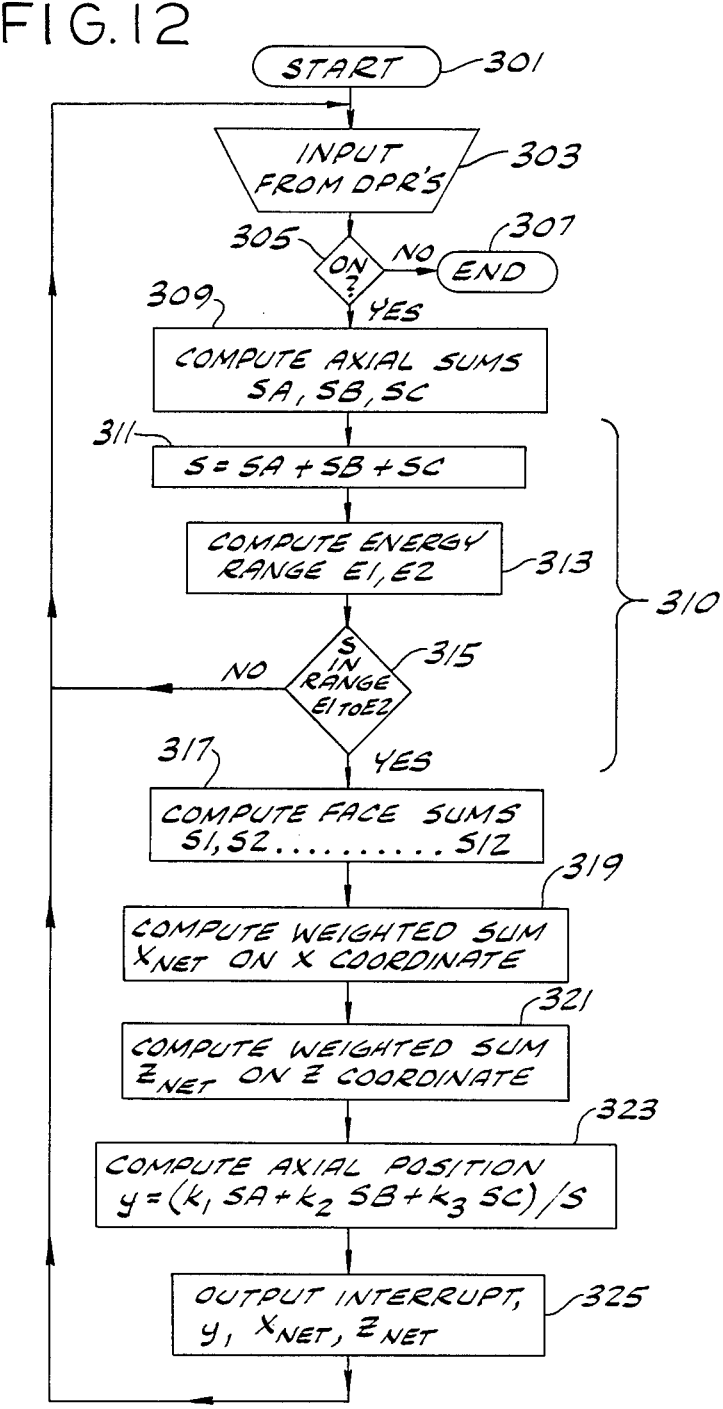
FIG. 12 is a flow diagram of operations of a digital logic circuit for computing energy and position in FIG. 11 in accordance with a method of the invention.

The operations of digital logic 255 are shown in FIG. 12. Operations commence at start 301 and input at step 303 the digital representations from DPRs 251 as soon as they are made available. At step 305, the digital logic 255 checks to determine if the switch 259 is on or off, and if off then end 307 is reached. If the switch is on, the digital logic 255 proceeds to compute the axial sums of equations 13, 14, and 15.

At steps 310, a test for a valid photon event 59 is made. Sum S is computed digitally from axial sums SA, SB, and SC in step 311. This step is a digital version of the operations accomplished by analog summer 115 of FIG. 6. Energy range values E1 and E2 are either recalled from store or calculated in step 313 for designating the range of energies that indicate a valid ionizing photon event 59. If sum S is in the range E1 to E2 at step 315, analogous to operation of circuit 127 of FIG. 6, operations proceed to step 317, otherwise they branch back to step 303.

At step 317, the sums S1, S2, ... S12 are computed digitally according to Equations 1, 2, ... 12.

Step 319 computes the position $X_{net}$ for the photon event 59 relative to the first coordinate X according to Equation 17 by computing a weighted sum as the difference of a first weighted sum of the sums of the outputs of units having the same positive value of the first coordinate position and a second weighted sum of the sums of the outputs of units having the same negative value of the first coordinate position; and the step 321 computes the position $Z_{net}$ for the photon event relative to the second coordinate Z according to Equation 18 by computing another weighted sum as the difference between a first weighted sum of the sums of the outputs of units having the same positive value of the second coordinate position and a second weighted sum of the sums of the outputs of units having the same negative value of the second coordinate position.

In step 323 a value of axial position y is computed according to Equation 20.

In summary, the digital logic 255 computes an axial position for the photon event as a weighted sum of the sums of the outputs of units having the same axial position in step 323, computes a position Xnet for the photon event relative to a first coordinate X perpendicular to the axis 55 as a weighted sum of the sums of the outputs of units having the same first coordinate X position in step 319, and in step 321 computes a position Znet for the photon event relative to a second coordinate Z perpendicular to the axis 55 as a weighted sum of the sums of the outputs of units having the same second coordinate Z position.

At step 325 digital logic 255 outputs an interrupt signal INT-bar to processor 257 and communicates the axial position y, and the weighted sums $X_{net}$ and $Z_{net}$, whence operations return to step 303 for computations relative to a new photon event.

Figure 13:
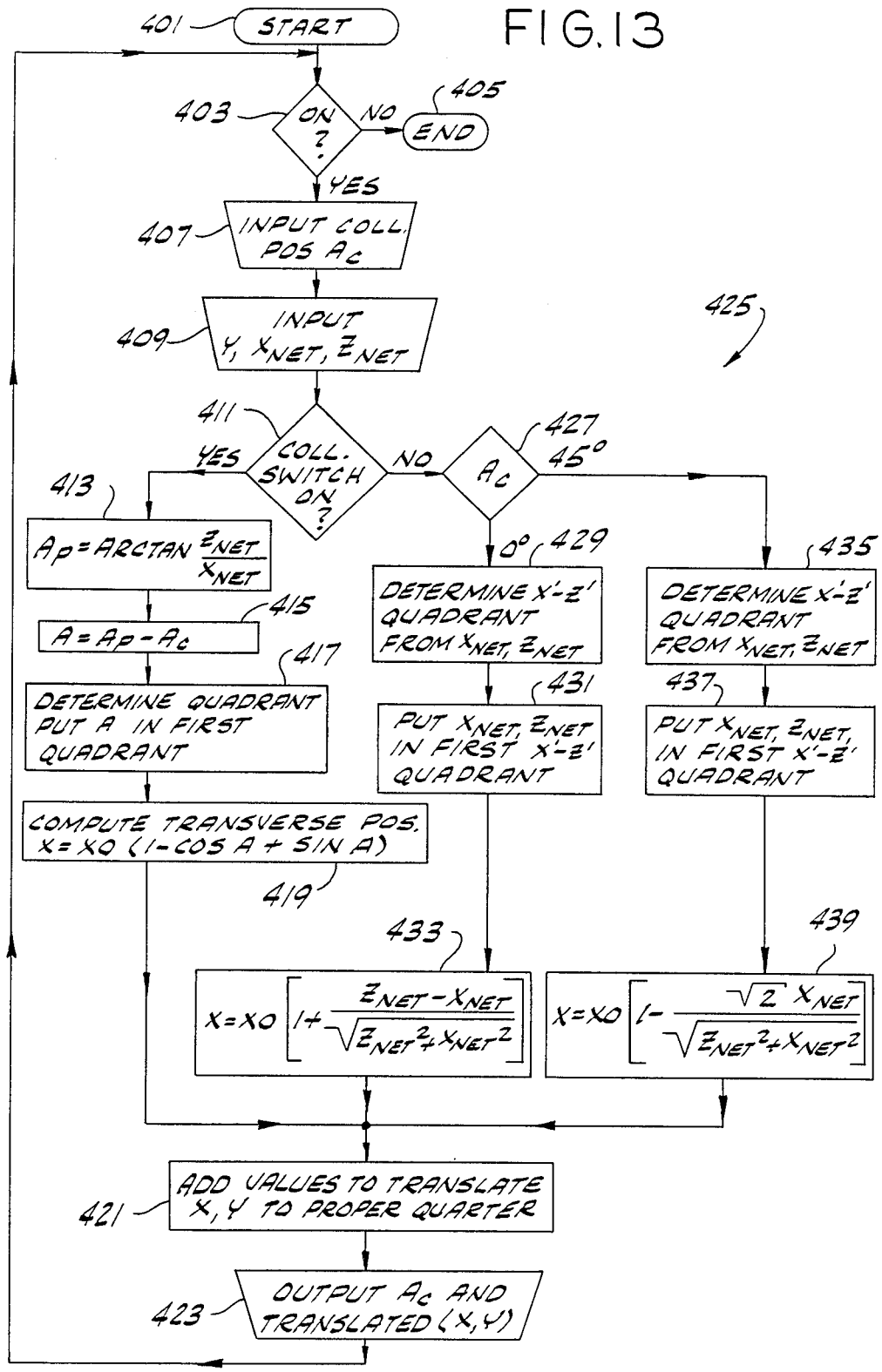
FIG. 13 is a flow diagram of operations of a single photon image processor of FIG. 11 according to a method of the invention.

In FIG. 13, the flow of operations of the single photon image processor 257 of FIG. 11 commences with START 401 and checks the On/Off switch 259 at step 403. If switch 259 is set to Off, operations terminate at END 405. If switch 259 is set to On, operations proceed to step 407 and the collimator position angle $A_c$ is input from encoder 58 of FIG. 1. Then at step 409, the axial position value y from digital logic 255 and the weighted sums $X_{net}$ and $Z_{net}$ are input in response to an interrupt INT-bar.

In step 411, processor 257 checks collimator angle mode switch 261. If switch 261 is on, processor 257 executes a routine capable of accomodating values of collimator angle $A_c$ from encoder 58 over a continuous range of rotation of collimator 51 of FIG. 1. The steps 413, 415, 417, 419, 421, and 423 are essentially the same as the steps 217, 233, 234, 235, 237, and 239 of FIG. 7 respectively and further discussion of them is omitted for brevity.

When the collimator angle mode switch 261 is switched off, operations branch from step 411 to a series of operations 425 for computing the transverse position x when the collimator angle $A_c$ is limited to the two values 0 and 45 degrees. Since photon event 59 can, of course, still occur in any quadrant of the X'-Z' coordinate system, the quadrant needs to be determined. The test used depends on whether the collimator angle is 0 or 45 degrees. Accordingly, the collimator angle $A_c$ is checked at step 427. If $A_c$ is zero, the X-Z and X'-Z' coordinate systems coincide and the quadrant of angle $A_p$ is the same as the quadrant of angle A. Then the following operations are performed in step 429 to determine the quadrant. In step 429, the positive or negative character of $X_{net}$ and $Z_{net}$ are tested. If both $X_{net}$ and $Z_{net}$ are positive, a quadrant identification 1 for first quadrant is assigned; if both are negative, identification 3 for third quadrant is assigned; if $Z_{net}$ is positive and $X_{net}$ is negative identification 2 for second quadrant is assigned; and if $X_{net}$ is positive and $Z_{net}$ is negative identification 4 for fourth quadrant is assigned.

With angle $A_c$ equal to zero, operations now proceed to step 431. Depending on the quadrant identification number assigned, operations are performed on the values of $X_{net}$ and $Z_{net}$ in a manner analogous to putting the angle $A_p$ in the first quadrant. If quadrant identification is 1, then operations pass directly to step 433; if quadrant identification is 2, $Z_{net}$ is made equal to the negative of $X_{net}$ input in step 409 and $X_{net}$ is made equal to the value of $Z_{net}$ input in step 409; if quadrant identification is 3, both $Z_{net}$ and $X_{net}$ are reversed in sign; and if quadrant identification is 4, $Z_{net}$ is made equal to the value of $X_{net}$ input in step 409 and $X_{net}$ is made equal to the negative of $Z_{net}$ input in step 409. After the justmentioned operations occur for quadrant identification 2, 3, or 4, step 433 is reached.

In step 433 a transverse position is calculated by an equation which accomplishes both an arctangent calculation and a $(1-\cos A + \sin A)$ calculation in one step given by the formula:

$$x = X0[1 + (Z_{net} - X_{net})/SQRT(Z_{net}^2 + X_{net}^2)] \qquad (22)$$

Step 433 constitutes computing in electrical form a value of position for at least one of the scintillations as a function of the first and second weighted sums $X_{net}$ and $Z_{net}$ for the first and second coordinates X and Z. Moreover, step 433 constitutes computing in electrical form a transverse position for at least one of the scintillations substantially proportional to the function $(1-\cos A+\sin A)$ where A is the difference between the arctangent of the ratio of the first and second weighted sums and an angular position of the collimating means. In addition step 433 constitutes computing in electrical form a transverse position for at least one of the scintillations substantially proportional to the sum of unity and the ratio of the difference of the first and second weighted sums to the square root of the sum of the squares of the first and second weighted sums. The computation is accomplished by executing coding for the mathematical steps, or made even more swift in processor 257 by implementing Equation 22 as a lookup table the rows and columns of which are addressed by values of $X_{net}$ and $Z_{net}$. After step 433 step 421 is reached.

If $A_c$ is 45 degrees at step 427 a branch is made to step 435. The X-Z and X'-Z' coordinate systems no longer coincide and the quadrant of angle $A_p$ is no longer the same as the quadrant of angle A as a general matter. Then the following operations are performed in step 435 to determine the quadrant in the X'-Z' coordinate system that the angle $A = A_p - 45°$ lies in. In step 435, the positive or negative character of $X_{net}$ and $Z_{net}$ and a comparison of their magnitudes are tested. If $Z_{net}$ is positive and $Z_{net}$ exceeds $X_{net}$ in magnitude, a quadrant identification 1 for first quadrant is assigned; if $Z_{net}$ is negative and $Z_{net}$ exceeds $X_{net}$ in magnitude, identification 3 for third quadrant is assigned; if $X_{net}$ is negative and $X_{net}$ exceeds $Z_{net}$ in magnitude, identification 2 for second quadrant is assigned; and if $X_{net}$ is positive and $X_{net}$ exceeds $Z_{net}$ in magnitude, identification 4 for fourth quadrant is assigned.

With angle $A_c$ equal to 45 degrees, operations now proceed to step 437. Depending on the quadrant identification number assigned, operations are performed on the values of $X_{net}$ and $Z_{net}$ in a manner analogous to putting the angle A in the first quadrant. If quadrant identification is 1, then operations pass directly to step 439; if quadrant identification is 2, $Z_{net}$ is made equal to the negative of $X_{net}$ input in step 409 and $X_{net}$ is made equal to the value of $Z_{net}$ input in step 409; if quadrant identification is 3, both $Z_{net}$ and $X_{net}$ are reversed in sign; and if quadrant identification is 4, $Z_{net}$ is made equal to the value of $X_{net}$ input in step 409 and $X_{net}$ is made equal to the negative of $Z_{net}$ input in step 409. After the justmentioned operations occur for quadrant identification 2, 3, or 4, step 439 is reached.

In step 439 a transverse position x for collimator angle $A_c$ equal to 45° is calculated by an equation which accomplishes both an arctangent calculation and a $(1-\cos A + \sin A)$ calculation in one step given by the formula:

$$tx = X0[1 - SQRT(2)X_{net}/SQRT(Z_{net}^2 + X_{net}^2)] \qquad (23)$$

Step 439 constitutes computing in electrical form a value of position for at least one of the scintillations as a function of the first and second weighted sums $X_{net}$ and $Z_{net}$ for the first and second coordinates X and Z. Moreover, step 433 constitutes computing in electrical form a transverse position for at least one of the scintillations substantially proportional to the function $(1-\cos A+\sin A)$ where A is the difference between the arctangent of the ratio of the first and second weighted sums and an angular position of the collimating means. In addition step 433 constitutes computing in electrical form a transverse position for at least one of the scintillations substantially proportional to unity less the product of the square root of two with the ratio of the first weighted sum to the square root of the sum of the squares of the first and second weighted sums. The computation is accomplished by executing coding for the mathematical steps, or made even more swift in processor 257 by implementing Equation 23 as a lookup table the rows and columns of which are addressed by values of $X_{net}$ and $Z_{net}$. After step 439 step 421 is reached.

In FIG. 13, the approach of steps 425 can be generalized for many collimator angles $A_c$. First, $X_{net}$ and $Z_{net}$ are transformed from the stationary X-Z coordinate system to the rotating X'-Z' system by the equations:

$$X_{net}' = X_{net}\cos A_c + Z_{net}\sin A_c \qquad (24)$$

$$Z_{net}' = Z_{net}\cos A_c - X_{net}\sin A_c \qquad (25)$$

Using $X_{net}'$ and $Z_{net}'$ from Equations 24 and 25 in place of $X_{net}$ and $Z_{net}$, processor 257 is programmed to execute the operations of steps 431 and 433 of FIG. 13. Computing the trigonometric cosine of $A_c$ and sine of $A_c$ is simplified by storing their values in a table for a preselected set of values of collimator angle $A_c$.

Figure 14:
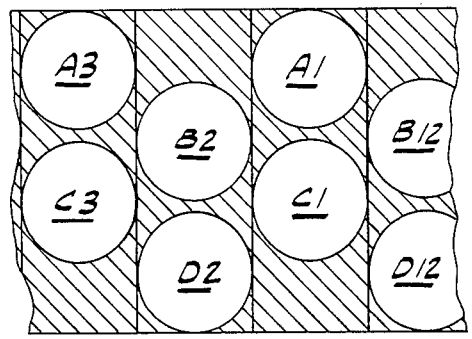
FIG. 14 is a depiction of an alternative embodiment of the invention utilizing photomultiplier tubes in staggered array around a tubular scintillation crystal.

In FIG. 14, an alternative embodiment of a detector-collimator assembly 23 of FIG. 1 is shown in which rows of PMTs, shown as circles, are staggered or offset in axial position relative to the PMTs in the adjacent rows. In FIG. 1, by contrast, the PMTs in each row are aligned with the PMTs in adjacent rows. The weighted sums are computed in a manner similar in principle to that accomplished in FIG. 6 and its equations 1-18. Axial sum SA is formed by summing FIG. 14 PMTs A1,A3,A5,A7,A9,A11. Sum SB is formed by summing B2,B4,B6,B8,B10,B12. Sum SC is the sum of outputs C1,C3,C5, C7,C9,C11. Sum SD is the sum of outputs D2,D4,D6,D8,D10,D12. Row sums S1 are formed by summing each pair of PMTs in each row. Row sum S1 is the sum of A1+C1 and row sum S2 is the sum of B2 and D2, and similarly around all twelve rows. The g constants g1, g2, and g3 for the FIG. 14 version are the same as in FIG. 6 and the k constants are recomputed for the embodiment of FIG. 14.

To do positron imaging in an embodiment of the invention shown in FIG. 15, a positron annihilation radiation imaging apparatus 500 has a detector assembly 501 similar to assembly 23 of FIG. 1 except that the collimator is omitted. As such, detector assembly 501 includes a substantially tubular body 503 of material capable of producing scintillations in response to bombardment by ionizing radiation and means for converting the scintillations to electrical outputs including a plurality of scintillation sensing units in the form of PMTs A1, B1, C1, ... A12, B12, C12 disposed both along and around the outside of the substantially tubular body 503. A set of preamplifiers 509 and DPRs 511 are provided for the PMTs in the same manner as preamplifiers 25 of FIG. 1 and DPRs 251 of FIG. 11. DPRs 511 feed a digital circuit 513 for computing energy and positions through 36 8-bit buses 515. The digital circuit 513 feeds information to a positron image processor 517 which in turns communicates pairs of values (x,y) for transverse and axial position and a "synthesized collimator" angle $A_c$ to bus 33. An On/Off switch 519 is provided for processor 517. Bus 33, digital real time display apparatus 35, film formatter equipment 37, SPECT computer 41, and ECT display 43 are the same as in FIG. 1.

A patient is administered a radiopharmaceutical specific for brain metabolism such as 2-Fluorodeoxyglucose labelled with fluorine-18, which decays by positron emission. The positrons emitted are annihilated microscopically near the brain site where the metabolism is occurring, and produce oppositely directed gamma rays 505 and 507 having an energy of 511 KeV.

Figure 16:
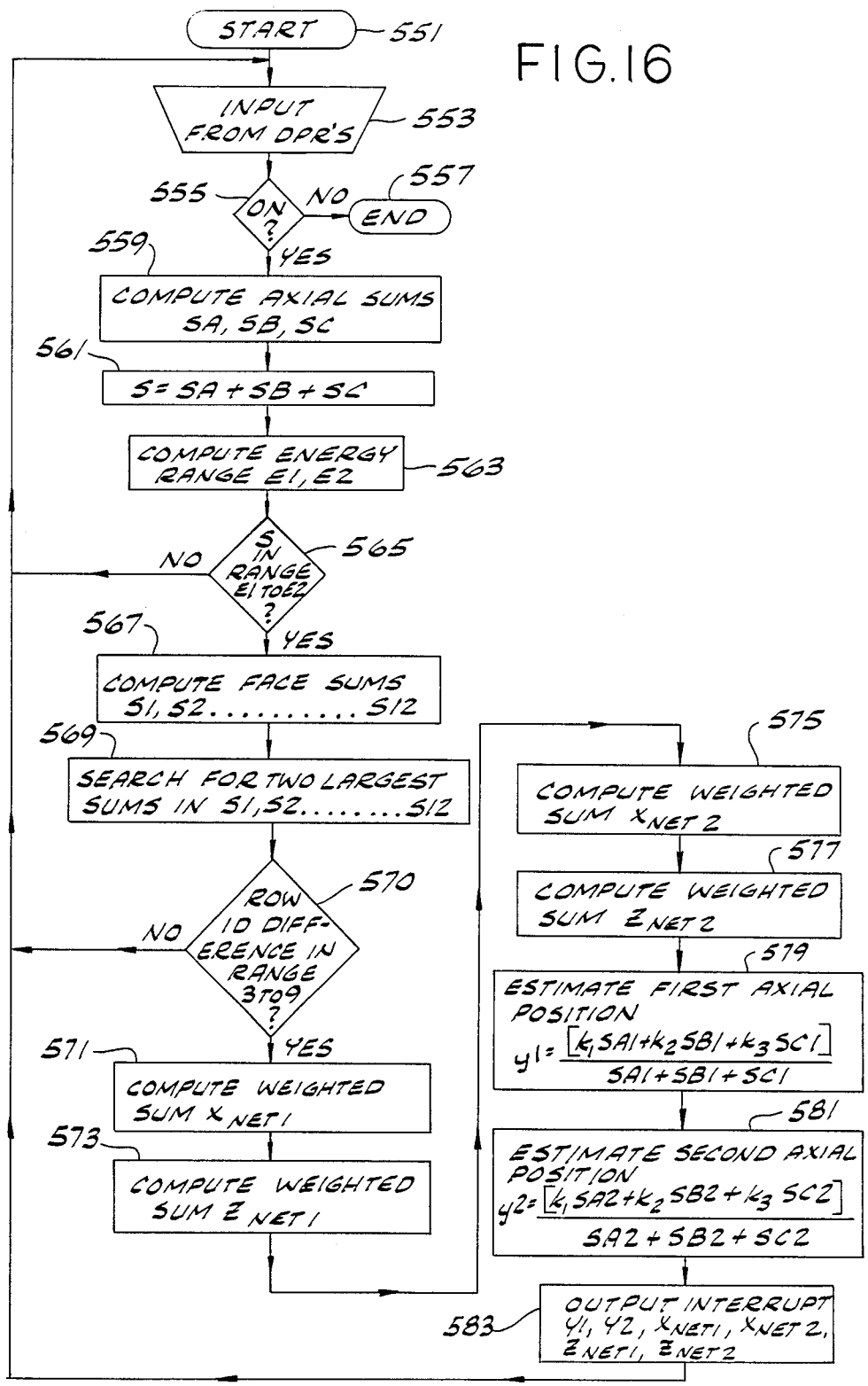
FIG. 16 is a flowchart of operations of a digital logic circuit for computing energy and positions in FIG. 15 in accordance with a method of the invention.

In FIG. 16, the operations for the digital logic circuit 513, which includes a microcomputer, commence at START 551. Steps 551, 553, 555, 557, 559, 561, 563, 565, and 567 are essentially the same as the already-described steps 301, 303, 305, 307, 309, 311, 313, 315, and 317 of FIG. 12 respectively. The energy range in step 565 is selected to bracket twice the 511 KeV value, or 1022 KeV, by nominally plus or minus 10%, thereby obviating a coincidence detection approach which can also be used but is believed to be more expensive to implement. Further discussion of the justmentioned steps is omitted for brevity.

At step 569, a search through the twelve row sums S1, S2, ... S12 is made and the row having the largest sum and the row having the second largest sum are identified with row identification numbers in the set 1 to 12. At step 570, the absolute value of the difference of the row identification numbers for the row having the largest sum and the row having the second largest sum is compared with a predetermined range such as being greater than or equal to 3 and less than or equal to 9. If the difference lies outside of the range, operations branch back to step 553 because light is commingling on at least one row from both photon events. If the difference lies within the range, operations proceed to step 571. It is noted that when the apparatus is scaled up for whole body imaging, utilizing 24 rows for example, the range selected to avoid commingling of light is changed to the range 5 to 19 (24 minus 5).

At step 571 an X coordinate position $X_{net1}$ is calculated using the sums for the row having the largest sum according to the following equation:

$$X_{net1} = g_1(S3+S10) + g_2(S2+S11) + g_3(S1+S12) - [g_1(S4+S9) + g_2(S5+S8) + g_3(S6+S7)] \quad (26)$$

In step 571, Equation 26 is computed by setting all values S1, S2, ... S12 to zero, except for the values S(I), $S((I+1)_{mod\ 12})$, and $S((I-1)_{mod\ 12})$ where I is the number of the row having the largest sum. For example, if row 3 has the largest sum S3, then the values S2, S3, and S4 are the only nonzero row sums utilized in equation 26, and equation 26 reduces to:

$$X_{net1} = g_1 S3 + g_2 S2 - g_1 S4 \quad (27)$$

For another example, if row 1 has the largest sum S1, then the values S1, S2, and S12 are the only nonzero row sums utilized in equation 22 (0 modulo 12 is 12), and equation 26 reduces to:

$$X_{net1} = g_2 S2 + g_3(S1+S12) \quad (28)$$

For yet another example, if row 12 has the largest sum S12, then the values S12, S11, and S1 are the only nonzero row sums utilized in equation 26 (13 modulo 12 is 1), and equation 26 reduces to:

$$X_{net1} = g_2 S11 + g_3(S1+S12) \quad (29)$$

At step 573 a Z coordinate position $Z_{net1}$ is calculated using the sums for the row having the largest sum according to the following formula:

$$Z_{net1} = g_1(S6+S1) + g_2(S5+S2) + g_3(S4+S3) - [g_1(S7+S12) + g_2(S8+S11) + g_3(S9+S10)] \quad (30)$$

In step 573, Equation 30 is computed by setting all values S1, S2, ... S12 to zero, except for the values S(I), $S((I+1)_{mod\ 12})$, and $S((I-1)_{mod\ 12})$ where I is the number of the row having the largest row sum. For example, if row 3 has the largest row sum S3, then the values S2, S3, and S4 are the only nonzero row sums utilized in equation 30, and equation 30 reduces to:

$$Z_{net1} = g_2 S2 + g_3(S4+S3) \quad (31)$$

For another example, if row 1 has the largest sum S1, then the values S1, S2, and S12 are the only nonzero row sums utilized in equation 30 (0 modulo 12 is 12), and equation 30 reduces to:

$$Z_{net1} = g_1 S1 + g_2 S2 - g_1 S12 \quad (32)$$

For yet another example, if row 12 has the largest sum S12, then the values S12, S11, and S1 are the only nonzero row sums utilized in equation 30 (13 modulo 12 is 1), and equation 30 reduces to:

$$Z_{net1} = g_1 S - g_1 S12 - g_2 S11 \quad (33)$$

At step 575 a second X coordinate position $X_{net2}$ is calculated using the sums for the row having the second largest value according to the following formula:

$$X_{net2} = g_1(S3+S10) + g_2(S2+S11) + g_3(S1+S12) - [g_1(S4+S9) + g_2(S5+S8) + g_3(S6+S7)] \quad (34)$$

In step 575, Equation 34 is computed analogously to Equation 26 of step 571 by setting all values S1, S2, ... S12 to zero, except for the values S(J), $S((J+1)_{mod\ 12})$, and $S((J-1)_{mod\ 12})$ where J is the number of the row having the second largest row sum.

In step 577 a second Z coordinate position $Z_{net2}$ is calculated using the sums for the row having the second largest value according to the following formula:

$$Z_{net2} = g_1(S6+S1) + g_2(S5+S2) + g_3(S4+S3) - [g_1(S7+S12) + g_2(S8+S11) + g_3(S9+S10)] \quad (35)$$

In step 577, Equation 35 is computed analogously to Equation 30 of step 573 by setting all values S1, S2, ... S12 to zero, except for the values S(J), S((J+1)$_{mod\ 12}$), and S((J−1)$_{mod\ 12}$) where J is the number of the row having the second largest sum.

The next steps 579 and 581 are performed for the purpose of obtaining estimated axial positions y1 and y2 for first and second photon events 59′ and 59″ in FIG. 15. In step 579 a first axial position y1 is calculated using the sums for the row having the largest value and its two adjacent rows according to the following equations:

$$SA1 = A1+A2+A3+A4+A5+A6+A7+A8+A9+A10+A11+A12 \quad (36)$$

$$SB1 = B1+B2+B3+B4+B5+B6+B7+B8+B9+B10+B11+B12 \quad (37)$$

$$SC1 = C1+C2+C3+C4+C5+C6+C7+C8+C9+C10+C11+C12 \quad (38)$$

In step 579, Equations 32, 33, and 34 are computed by setting all values A1 through A12 to zero, all values B1 through B12 to zero, and all values C1 through C12 to zero, except for the values A(I), A((I+1)$_{mod\ 12}$), and A((I−1)$_{mod\ 12}$), B(I), B((I+1)$_{mod\ 12}$), and B((I−1)$_{mod\ 12}$), and C(I), C((I+1)$_{mod\ 12}$), and C((I−1)$_{mod\ 12}$), where I is the number of the row having the largest sum. For example, if row 3 has the largest sum, then the values A2,A3,A4,B2,B3,B4,C2,C3,and C4 are the only DPR outputs utilized in equations 36,37, and 38, which reduce to:

$$SA1 = A2+A3+A4 \quad (39)$$

$$SB1 = B2+B3+B4 \quad (40)$$

$$SC1 = C2+C3+C4 \quad (41)$$

For another example, if row 1 has the largest sum, then the values A1,A2,A12,B1,B2,B12,C1,C2,and C12 are the only DPR outputs utilized in the equations 36, 37, and 38 (0 modulo 12 is 12), which reduce to:

$$SA1 = A1+A2+A12 \quad (42)$$

$$SB1 = B1+B2+B12 \quad (43)$$

$$SC1 = C1+C2+C12 \quad (44)$$

For yet another example, if row 12 has the largest sum, then the values A12,A11,A1,B12,B11,B1,C12,C11, and C1 are the only nonzero DPR outputs utilized in equations 36,37, and 38 (13 modulo 12 is 1), which reduce to:

$$SA1 = A1+A11+A12 \quad (45)$$

$$SB1 = B1+B11+B12 \quad (46)$$

$$SC1 = C1+C11+C12 \quad (47)$$

The calculations in step 579 are concluded by computing the first axial position y1 according to the formula:

$$y1 = [k_1 SA1 + k_2 SB1 + k_3 SC1]/[SA1+SB1+SC1] \quad (48)$$

The constants $k_1$, $k_2$, and $k_3$ are obtained from geometric considerations of solid angles subtended by the PMTs relative to various positions in the tubular scintillation body 503 and have values identical to those determined for use in the single photon image processor 31.

In step 581 a second axial position y2 is calculated using the sums for the row having the second largest row sum according to the following formulas:

$$SA2 = A1+A2+A3+A4+A5+A6+A7+A8+A9+A10+A11+A12 \quad (49)$$

$$SB2 = B1+B2+B3+B4+B5+B6+B7+B8+B9+B10+B11+B12 \quad (50)$$

$$SC2 = C1+C2+C3+C4+C5+C6+C7+C8+C9+C10+C11+C12 \quad (51)$$

In step 581, Equations 49, 50, and 51 are computed analogously to Equations 36, 37, and 38 by setting all values A1 through A12 to zero, all values B1 through B12 to zero, and all values C1 through C12 to zero, except for the values A(J), A((J+1)$_{mod\ 12}$), and A((J−1)$_{mod\ 12}$), B(J), B((J+1)$_{mod\ 12}$), and B((J−1)$_{mod\ 12}$) 12), and C(J), C((J+1)$_{mod\ 12}$), and C((J−1)$_{mod\ 12}$), where J is the number of the row having the second largest row sum.

The calculations in step 581 are concluded by computing the second axial position y2 according to the formula:

$$y2 = [k_1 SA2 + k_2 SB2 + k_3 SC2]/[SA2+SB2+SC2] \quad (52)$$

In step 583 digital logic 513 outputs an interrupt INT-bar to processor 517 and communicates the values y1, $X_{net1}$, $Z_{net1}$ for photon event 59′ and the values y2, $X_{net2}$, $Z_{net2}$ for photon event 59″ to processor 517.

Positron image processor 517, generally speaking, produces axial and transverse position values (x,y) from the just-mentioned information communicated to it and computes an angle $A_c$ analogous to collimator angle $A_c$ to interface with the SPECT computer 43. It is to be understood that all of the pairs of values (y1, $X_{net1}$, $Z_{net1}$), (y2, $X_{net2}$, $Z_{net2}$) can be stored in available megabyte memory in a list mode acquisition technique, and the SPECT computer can be programmed for tomographic reconstruction using all such values according to a procedure adapted for positron annihilation imaging and different from that applied for single photon imaging. The list mode acquisition technique preserves and permits use of all positron annihilation event data even when the photon pairs emitted therefrom are oblique to the Y axis. However, in the discussion that follows, the positron image processor 517 performs a "collimation" procedure which utilizes only ionizing photon pairs such as 505 and 507 which are emitted substantially perpendicular to the Y axis.

Figure 17:
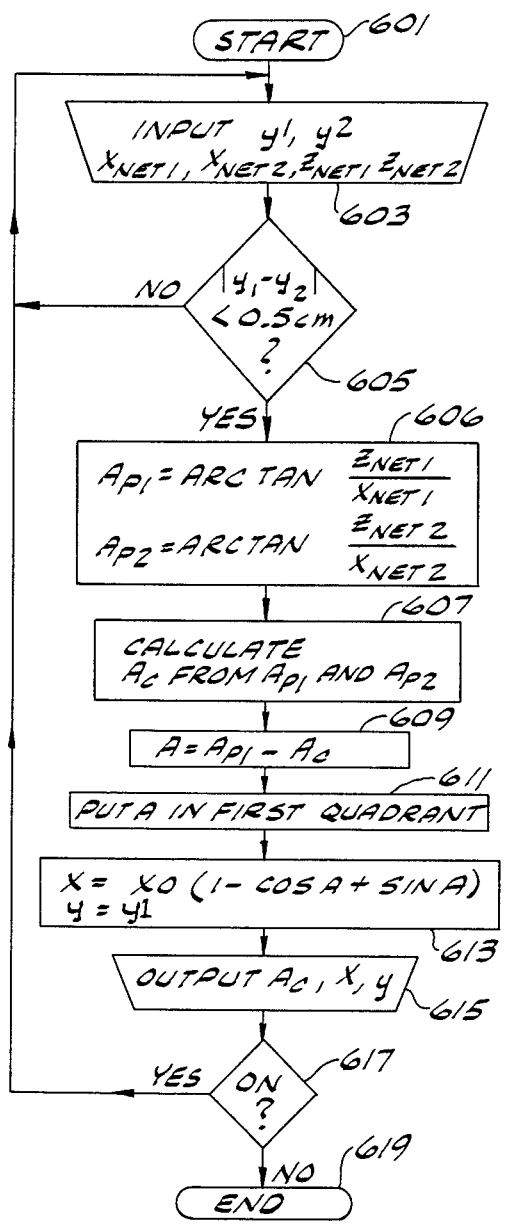
FIG. 17 is a flowchart of operations of a positron image processor in FIG. 15 in accordance with a method of the invention.

FIG. 17 shows the operations of positron image processor 517, which begin at START 601. The values (y1, $X_{net1}$, $Z_{net1}$) and (y2, $X_{net2}$, $Z_{net2}$) are input at step 603.

Positron image processor 517 selects at step 605 only those data having y1 and y2 being substantially equal so that the difference y2−y1 is in magnitude less than or equal to a predetermined value of 5% of the length of the scintillation crystal for head imaging or about 0.5 centimeter for either head or body imaging.

The estimated Y position on axis 55 of the positron annihilation event is output as y1, although the value y2 or any Y value between them may be alternatively chosen for output.

In step 606 respective first and second angular position values for first and second photon events 59' and 59" resulting from the positron annihilation event are calculated according to the formulas:

$$A_{p1} = \text{Arctan}(Z_{net1}/X_{net1}) \quad (53)$$

$$A_{p2} = \text{Arctan}(Z_{net2}/X_{net2}) \quad (54)$$

Next an angle $A_c$ analogous to a collimator angle in single photon imaging is calculated in positron annihilation imaging in step 607. The manner of the calculation in step 607 is discussed in more detail in the next paragraph and in connection with FIGS. 18A, 18B, and 19. When angle $A_c$ is obtained in step 607, then angle value A is computed as the difference of an arbitrarily selected one of angles $A_{p1}$ and $A_{p2}$ and the angle $A_c$. In step 609 angle A is set equal to angle $A_{p1} - A_c$. In step 611 angle A is translated into the quadrant in the same manner as described for step 234 of FIG. 7. In step 613 a transverse position value x for the positron annihilation event is computed according to the formula X0(1−cos A+sin A) in the same manner as in step 235 in FIG. 7. Also in step 613, an axial position y of the positron annihilation event is set equal to y1, which is an arbitrarily selected one of positions y1 and y2. In step 615 values of the angle $A_c$ analogous to a collimator angle, and the pair (x,y) of transverse and axial position values are output onto bus 33. These values $A_c$, x, and y are compatible with the digital real time display 35, film formatter 35, SPECT computer 41 and ECT display 43 because they can be used in the same manner as the corresponding $A_c$, x, and y values from the single photon radiation imaging apparatus 21 of FIG. 1. At step 617, switch 519 of FIG. 15 is checked, and if On then operations branch back to step 603 and if Off then END 619 is reached.

Figure 18A:
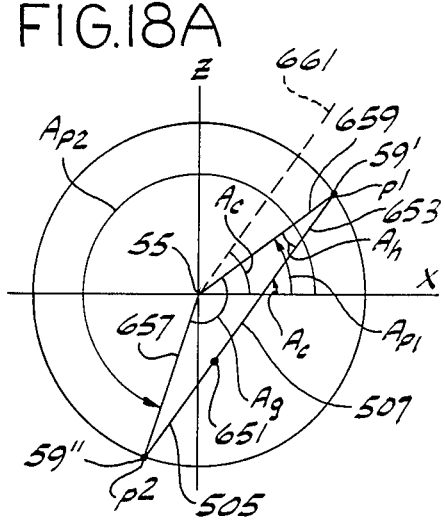
FIGS. 18A and 18B are diagrams of first and second photon events resulting from positron annihilation with geometric construction lines for computing an angle value $A_c$ describing the path of photons leaving a positron annihilation event.

FIG. 18A shows a first geometric construction for explaining the "synthesized collimator" angle $A_c$ calculation in step 607 of FIG. 17. Positron annihilation event 651 produces collinear, oppositely directed ionizing photons traveling in collinear paths 505 and 507, which in turn result in photon events 59' and 59", also designated p1 and p2. The designation "p1" is given to the point having the smaller angle measured counterclockwise from the X axis. A line 653 defined by collinear paths 505 and 507 forms an angle with the X axis which is identified as the "synthesized collimator" angle $A_c$.

The geometric construction proceeds as follows. Construct lines 657 and 659 respectively from the origin (the axis 55) to points p2 and p1. These lines 659 and 657 are oriented relative to the X axis at respective angles designated $A_{p1}$ and $A_{p2}$. Define the angle $A_g$ as the internal angle at the vertex at the origin for the triangle defined by the points p1, p2 and the origin.

Since the triangle is an isosceles triangle, the angle $A_h$ at the vertex defined by point p1 is equal to half the quantity 180 degrees less angle $A_g$. Construct a line 661 through the origin parallel to the line 653 joining points p1 and p2. From geometric considerations line 661 is oriented at the angle $A_c$ relative to the X axis the same as line 653. By inspection of line 661, angle $A_c$ is equal to the sum of the angle $A_{p1}$ and the angle $A_h$. The foregoing reasoning results in a formula for $A_g$ (where ABS means absolute value, or magnitude) and for angle $A_c$ given as:

$$A_g = 360° - \text{ABS}(A_{p2} - A_{p1}) \quad (55)$$

$$A_c = A_{p1} + (180° - A_g)/2 \quad (56)$$

Figure 18B:
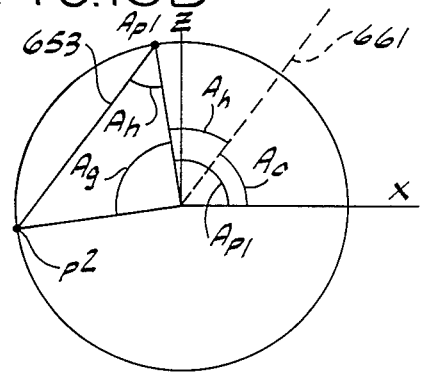

FIG. 18B shows another example of a triangle formed by photon events p1 and p2 and the origin. Angles $A_g$, $A_h$, $A_{p1}$, and $A_c$ are drawn with corresponding meanings to the correspondingly marked angles in FIG. 18A. In FIG. 18B geometric construction shows that $A_c$ is equal to angle $A_{p1}$ less angle $A_h$. Angles $A_g$ and $A_c$ are given by the formulas:

$$A_g = \text{ABS}(A_{p2} - A_{p1}) \quad (57)$$

$$A_c = A_{p1} - (180° - A_g)/2 \quad (58)$$

The foregoing equations 55 through 58 are implemented in electrical form in step 607 of FIG. 17.

Figure 19:
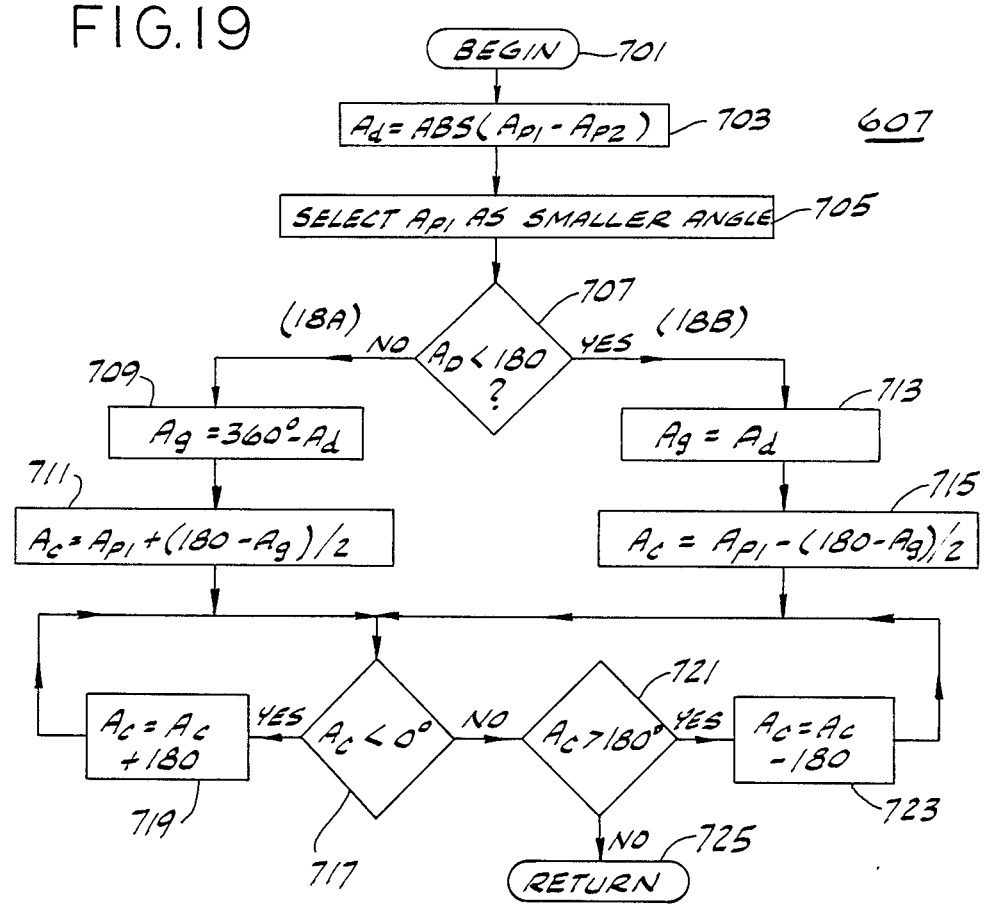
FIG. 19 is a flowchart of operations of the positron image processor in FIG. 15 in producing a "synthesized collimator" angle $A_c$ in FIG. 17 in accordance with a method of the invention

In executing step 607 of FIG. 17, a flow of operations in FIG. 19 is performed commencing at BEGIN 701 and proceeding to compute a difference angle $A_d$ as the absolute value of the difference between angles $A_{p1}$ and $A_{p2}$ in step 703. In step 705, the smaller angle of $A_{p1}$ and $A_{p2}$ is identified and designated $A_{p1}$ thereafter. In step 707 the difference angle $A_d$ is tested. If $A_d$ exceeds 180°, the diagram of FIG. 18A pertains and step 709 is reached, otherwise the diagram of FIG. 18B pertains and step 711 is reached. In step 709 the vertex angle $A_g$ is calculated according to equation 55, and in step 711 $A_g$ is calculated by equation 57. The "synthesized collimator" angle $A_c$ is computed at step 713 by equation 56 and at step 715 by equation 58 depending on the result of the test in step 707. Values of angle $A_c$ lying outside the range 0 to 180 degrees are translated into that range by steps 717, 719, 721 and 723. In step 717 the value of $A_c$ is checked for sign, and if negative, it is increased by 180° in step 719 until it is not negative. In step 721 the value of $A_c$ is checked for excess over 180°, and if excessive, it is decreased by 180° in step 723 until it is less than 180°, whence RETURN 725 is reached.

When $A_c$ is produced as just described, it remains to calculate the estimated transverse position of the positron annihilation event in FIG. 17. This is accomplished in essentially the same manner as for single photon imaging because the same information is present. Choose either one of $A_{p1}$ and $A_{p2}$, e.g. $A_{p1}$, without loss of generality. Then using the two values $A_c$ and $A_{p1}$, form the angle $A = A_{p1} - A_c$ in step 609. Discussion of the other steps 611 and 615 is found elsewhere hereinabove.

The radiation imaging apparatus of FIGS. 1 and 15 is increased in scale for imaging of the whole human body. A tubular scintillation body 57 of nominally 24" inside diameter, 12" length, and 0.5" thickness is made and surrounded with 24 rows of PMTs with 6 PMTs per row. Two adjacent 6" long tubular bodies with 3 PMTs per row can also be used. The patient table of FIG. 2 is longitudinally and vertically indexed for positioning the patient in the field of view of the system. Longitudinal motion of the patient table is selected to be either stepwise or continuous for both tomographic and nontomographic imaging. Because of the quadriplanar collimator and collection of data in four viewing planes simultaneously, the time required for whole-body imaging is advantageously brief.

Computation of g and k Constants

Figure 20:
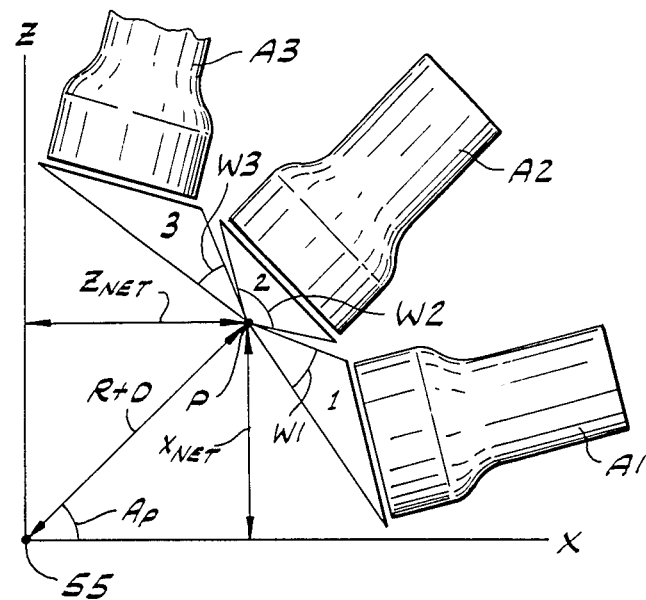
FIG. 20 is a simplified cross-section perpendicular to the longitudinal axis of the detector-collimator assembly of FIG. 1 showing geometrical construction lines used in computation of certain weighting (g) constants.
Figure 21:
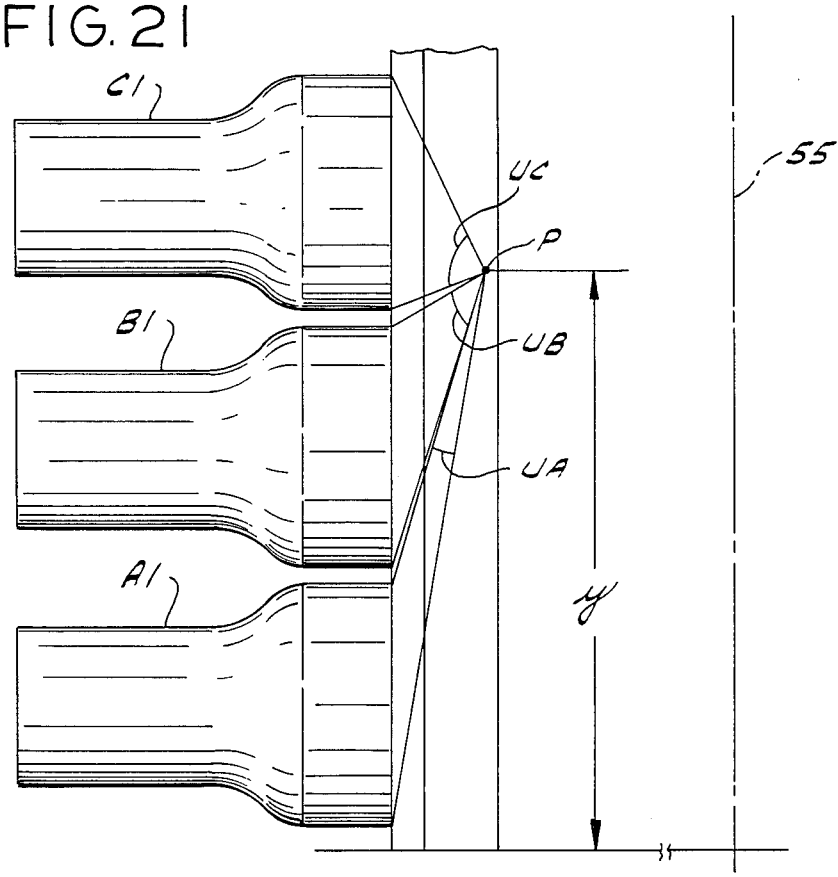
FIG. 21 is a simplified cross-section through the longitudinal axis of the detector-collimator assembly of FIG. 1 showing geometrical construction lines used in computation of certain weighting (k) constants.

FIG. 20 shows a simplified cross-section perpendicular to the axis 55 of the detector-collimator assembly 23 of FIG. 1. FIG. 21 shows a simplified cross-section through the axis 55 of the detector-collimator assembly of FIG. 1. FIGS. 20 and 21 are intended to suggest scale drawings which are prepared by the skilled worker so as to accurately represent the actual dimensions, angular relationships, and clearances in the assembly 23 when an embodiment is constructed. The purpose of such scale drawings is to assist in graphically determining values which are used in calculating the constants $g_1$, $g_2$, and $g_3$.

The mean depth of penetration D of the ionizing radiation in the scintillation crystal given the energy of the radiation is obtained. For example, the mean depth D for a energy value of 140 kev (typical of technetium-99m, Tc-99m, frequently used in nuclear medicine applications) is about 3.0 millimeters.

A planar angle proportional to the solid angle subtended by any one PMT relative to a given photon event point P is determined. This is accomplished by first recognizing that in general the circular face of a PMT projects an ellipse as seen from photon event point P. The ellipse has two perpendicular axes, a major axis and a minor axis. In the discussion which follows, it is of interest to determine the solid angle subtended by the ellipse as viewed from the photon event point P. This involves conceptually projecting the ellipse onto a hypothetical spherical surface centered on photon event point P in order to compute the solid angle subtended. While this would appear to be a formidable task to compute, the axes of the ellipse for PMT A1 of FIGS. 20 and 21, for example, are proportional in length to angles w1 and uA in FIGS. 20 and 21 respectively.

The g constants are calculated from the angles which are also proportional to the relative amounts of light reaching the PMTs from photon events at different points exemplified by point P, as determined by the angular constructions or projections shown in FIG. 20. This avoids setting up a complicated closed-form integration problem if analytical methods were used. An example of one such determination is now discussed.

In FIG. 20 angles w1, w2, w3, . . . w12 for the rows are regarded as being proportional to the S1, S2, S3, . . . S12 sums which would occur as a result of the photon event at point P. Conveniently, many of the sums are zero due to the cylindrical geometry of the scintillation body 57 which blocks the direct line of sight from the photon event point P to most of the PMTs. The angle values w can be graphically determined so that the values proportional to the S sums can be determined, and then these can be substituted into the $X_{net}$ and $X_{net}$ equations which involve the g constants. Because the location of each point P in the graphical procedure is selected a priori, $X_{net}$ and $X_{net}$ are merely the X and Z coordinate positions of the selected locations. Thus $X_{net}$ and $Z_{net}$ are knowns. Then the $X_{net}$ and $Z_{net}$ equations are solved in reverse, so to speak, to obtain the g constants. Equations 17 and 18 are repeated as follows:

$$X_{net}=g_1(S3+S10)+g_2(S2+S11)+g_3(S1+S12)-[g_1(S4+S9)+g_2(S5+S8)+g_3(S6+S7)] \quad (17)$$

$$Z_{net}=g_1(S6+S1)+g_2(S5+S2)+g_3(S4+S3)-[g_1(S7+S12)+g_2(S8+S11)+g_3(S9+S10)] \quad (18)$$

Arbitrarily locate a first photon event point P1 beneath face number 2 of FIG. 20 without loss of generality. The equations 17 and 18 then reduce to the following ("P1" being appended to identify quantities):

$$X_{netP1}=g_1w3P1+g_2w2P1+g_3w1P1 \quad (59)$$

$$Z_{netP1}=g_1w1P1+g_2w2P1+g_3w3P1 \quad (60)$$

where $$X_{netP1}=(R+D)\cos A_{P1} \quad (61)$$

and $$Z_{netP1}=(R+D)\sin A_{P1} \quad (62)$$

Next arbitrarily locate a second photon event point P2 elsewhere beneath face number 2, which results, in two more equations as follows ("P2" being appended to identify quantities):

$$X_{netP2}=g_1w3P2+g_2w2P2+g_3w1P2 \quad (63)$$

$$Z_{netP2}=g_1w1P2+g_2w2P2+g_3w3P2 \quad (64)$$

where $$X_{netP2}=(R+D)\cos A_{P2} \quad (65)$$

and $$Z_{netP2}=(R+D)\sin A_{P2} \quad (66)$$

The angles w1, w2, and w3 are measured graphically on the scale drawing for each point P1 and P2 (for a total of 6 measured angles). The angle $A_P$ is measured graphically for the two points P1 and P2. Now the eight equations 59 through 66 can be solved simultaneously by substituting 61, 62, 65, and 66 into 59, 60, 63, and 64 respectively to yield four equations in three unknowns. Since any selected one of the equations is redundant, it is ignored, and the other three equations are solved simultaneously for $g_1$, $g_2$, and $g_3$. In a detector-collimator assembly 23 of FIG. 1 having $(R+D)=15.3$ cm., $R=15.0$ cm., and radial distance to each PMT=17.0 cm., $g_1$, $g_2$, and $g_3$ are calculated to be 0.0703, 0.1920, and 0.2595 respectively.

The k constants are calculated by the graphical constructions or projections as shown in FIG. 21 from each of three points P1, P2, P3 each being as exemplified by point P of FIG. 21. Each point P1, P2, P3 has a different axial position Y.

The concept of the graphical construction is to regard angles uA, uB, and uC as being proportional to the SA, SB and SC values which would theoretically occur as a result of a photon event at point P. Axial position Y is a known when an event point P is selected and marked on the scale drawing, and the angle values uA, uB, and uC can be graphically determined. The axial position equation 20 is solved in reverse, so to speak, to obtain the k constants. Equation 20 is repeated as follows:

$$y=k_1SA+k_2SB+k_3SC \quad (20)$$

Arbitrarily locate three photon event points P1, P2, and P3 on the scale drawing. This results in three equations in three unknowns as follows ("P1", "P2", "P3" being appended to identify quantities):

$$yP1 = k_1 uAP1 + k_2 uBP1 + k_3 uCP1 \qquad (67)$$

$$yP2 = k_1 uAP2 + k_2 uBP2 + k_3 uCP2 \qquad (68)$$

$$yP3 = k_1 uAP3 + k_2 uBP3 + k_3 uCP3 \qquad (69)$$

The angles uA, uB, and uC are measured graphically for each of the three event points P1, P2, P3 on the scale drawing. Now the three equations 67 through 69 are solved simultaneously for $k_1$, $k_2$, and $k_3$. In a detector collimator assembly 23 of FIG. 1 having PMTs with 7.62 cm. diameter and center-to-center spacing of 8.57 cm., and perpendicular distance of 1.7 cm from photon events to faces of the PMTs, $k_1$, $k_2$, and $k_3$ are calculated to be 0.113, 0.357, and 0.582 respectively.

It is to be noted that the g and k constants may have some nonlinearity as a function of photon event location. Accordingly, the linear approach discussed above is suitably corrected or tuned by the skilled worker by experiment.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Radiation imaging apparatus comprising a tubular and optically continuous body of material for producing scintillations in response to bombardment by ionizing radiation; means for converting the scintillations to electrical outputs including a plurality of scintillation sensing units disposed both along and around the outside of the tubular and optically continuous body; and means for collimating the ionizing radiation for said tubular and optically continuous body with at least one group of parallel, outwardly directed, straight channels, which group is distributed over part of the width inside said tubular and optically continuous body and over a distance along the inside of said tubular and optically continuous body approximately encompassing lengthwise the plurality of scintillation sensing units disposed along the outside, said group of channels passing the ionizing radiation outward into said tubular and optically continuous body in only parallel directions.

2. Radiation imaging apparatus as set forth in claim 1 wherein the tubular body is composed of a crystalline material selected from the group consisting of sodium iodide and bismuth germanate.

3. Radiation imaging apparatus as set forth in claim 1 wherein said means for collimating the ionizing radiation has a substantially tubular structure positioned within said tubular body substantially coaxial therewith.

4. Radiation imaging apparatus as set forth in claim 1 wherein said collimating means provides four mutually perpendicular directions of collimation.

5. Radiation imaging apparatus as set forth in claim 1 wherein said converting means includes at least eight groups of at least two axially disposed units each, the at least eight groups of units being circumferentially disposed around the tubular body.

6. Radiation imaging apparatus as set forth in claim 5 wherein said converting means includes exactly twelve groups of at least two axially disposed units each.

7. Radiation imaging apparatus as set forth in claim 5 wherein each group has at least three axially disposed units aligned with the units in the other groups.

8. Radiation imaging apparatus as set forth in claim 5 wherein the units of each group are staggered in axial position relative to the units in the groups adjacent thereto.

9. Radiation imaging apparatus as set forth in claim 8 further comprising light transmissive means having substantially planar exterior faces surrounding said tubular body, each unit of said converting means being urged against one of the planar exterior faces of said light transmissive means.

10. Radiation imaging apparatus as set forth in claim 1 further comprising a tubular element which is substantially transparent to the ionizing radiation and substantially opaque to light, said tubular element surrounding said collimating means and being located between said collimating means and said tubular body.

11. Radiation imaging apparatus as set forth in claim 1 wherein said collimating means has at least one direction of collimation and said apparatus further comprises means for computing axial and transverse positions of the scintillations, the transverse positions being computed in electrical form as positions in at least one viewing plane perpendicular to the at least one direction of collimation.

12. Radiation imaging apparatus as set forth in claim 1 wherein said tubular body and said collimating means have a common axis and said sensing units have positions relative to first and second coordinates perpendicular to the axis, and said apparatus further comprises processing means including means for computing in electrical form a weighted sum of the sums of the outputs of units having the same position relative to the first coordinate, and for computing in electrical form a weighted sum of the sums of the outputs of units having the same position relative to the second coordinate.

13. Radiation imaging apparatus as set forth in claim 12 wherein said processing means comprises analog summing means.

14. Radiation imaging apparatus as set forth in claim 12 wherein said processing means comprises means for also computing an angular position for at least one of the scintillations substantially as the arctangent of the ratio of the weighted sums for the first and second coordinates.

15. Radiation imaging apparatus as set forth in claim 14 wherein said processing means comprises analog summing means for computing the weighted sums and digital computing means for computing the arctangent, said digital computing means being fed by said analog summing means.

16. Radiation imaging apparatus as set forth in claim 1 further comprising means for computing an angular position for at least one of the scintillations and computing a position value substantially proportional to $(1 - \cos A + \sin A)$ where A is the difference between an angular position for the at least one scintillation and the angular position of said collimating means.

17. Radiation imaging apparatus as set forth in claim 16 further comprising means for generating a tomographic display utilizing position value information produced by said computing means.

18. Radiation imaging apparatus as set forth in claim 1 wherein said units have respective axial positions, and said apparatus further comprises means for computing a position value for at least one of the scintillations substantially proportional to a weighted sum of the sums of the outputs of units having the same axial position divided by the sum of the axial sums.

19. Radiation imaging apparatus as set forth in claim 1 further comprising processing means for computing values of axial and transverse position for the scintillations.

20. Radiation imaging apparatus as set forth in claim 19 for use with a specimen and further comprising means for producing at least one representation of the specimen from the values of axial position and transverse position computed by the processing means for the scintillations.

21. Radiation imaging apparatus as set forth in claim 20 wherein said collimating means provides a plurality of directions of collimation and said processing means comprises means for also adding at least one predetermined value to some of the values of axial position and transverse position to cause said representation to show distinct views of the specimen as viewed along at least two of the directions of collimation.

22. Radiation imaging apparatus as set forth in claim 1 further comprising processing means for also summing all of the outputs of said converting means occurring at any one time, comparing the sum so obtained with a predetermined range, and, only if the sum so obtained is within the range, producing imaging information corresponding to the outputs at that time.

23. Radiation imaging apparatus for use with a substantially tubular body having an axis and composed of a material for producing scintillations in response to bombardment by ionizing radiation, and means for converting the scintillations to electrical outputs, including a plurality of scintillation sensing units disposed both along and around the outside of the tubular body and having axial positions and positions relative to first and second coordinates perpendicular to the axis, the radiation imaging apparatus comprising:
  first means for computing in electrical form a first weighted sum of the sums of the outputs of units having the same position relative to the first coordinate perpendicular to the tubular body axis, and for computing in electrical form a second weighted sum of the sums of the outputs of units having the same position relative to the second coordinate perpendicular to the tubular body axis; and
  second means for computing in electrical form a value of position around the tubular body for at least one of the scintillations as a function of the first and second weighted sums for the first and second coordinates perpendicular to the tubular body axis.

24. Radiation imaging apparatus as set forth in claim 23 wherein said first computing means comprises analog summing means and said second computing means comprises digital computer means fed by said analog summing means.

25. Radiation imaging apparatus as set forth in claim 23 further for use with collimating means positioned within the tubular body wherein said second computing means comprises means for also computing in electrical form a scintillation position value substantially proportional to $(1-\cos A + \sin A)$ where $A$ is the difference between the arctangent of the ratio of the weighted sums and an angular position of said collimating means.

26. Radiation imaging apparatus as set forth in claim 23 wherein said first computing means comprises means for also computing in electrical form sums of the outputs of units having the same axial position.

27. Radiation imaging apparatus as set forth in claim 26 wherein said second computing means comprises means for also computing in electrical form a position value for at least one of the scintillations substantially proportional to a weighted sum of the axial sums from said first computing means divided by the sum of the axial sums.

28. Radiation imaging apparatus as set forth in claim 23 wherein said second computing means comprises means for also generating signals representing an axial position and a transverse position for the at least one scintillation.

29. Radiation imaging apparatus as set forth in claim 28 further comprising means for generating a tomographic display utilizing the signals representing axial position and transverse position generated by the second computing means for a plurality of the scintillations.

30. Radiation imaging apparatus as set forth in claim 28 for use with a specimen emitting ionizing radiation from within the tubular body, the radiation imaging apparatus further comprising means for producing at least one representation of the specimen utilizing the signals representing axial position and transverse position generated by the second computing means for a plurality of the scintillations.

31. Radiation imaging apparatus as set forth in claim 28 wherein said second computing means comprises means for also generating other signals representing another axial position and another transverse position to which a predetermined value has been added.

32. Radiation imaging apparatus as set forth in claim 23 wherein said first computing means comprises means for also summing all of the outputs of said converting means, comparing the sum so obtained with a predetermined range, and, only if the sum so obtained is within the range, producing further information corresponding to at least one of the scintillations.

33. A radiation imaging method for use with a substantially tubular body having an axis and producing scintillations in response to bombardment by ionizing radiation, and means for converting the scintillations to electrical outputs including a plurality of scintillation sensing units disposed both along and around the outside of the tubular body and having axial positions and positions relative to first and second coordinates perpendicular to the axis, the method comprising the steps of:
  computing in electrical form a weighted sum of the sums of the outputs of units having the same position relative to the first coordinate;
  computing in electrical form a weighted sum of the sums of the outputs of units having the same position relative to the second coordinate; and
  computing in electrical form an angular position for at least one of the scintillations as the arctangent of the ratio of the weighted sums for the first and second coordinates.

34. The method as set forth in claim 33 wherein the steps of computing weighted sums in electrical form are accomplished by analog summing and the step of computing the arctangent is accomplished digitally.

35. The method as set forth in claim 33 further for use with collimating means having an angular position inside the tubular body, the method further comprising the step of computing in electrical form a position value substantially proportional to (1-cos A+sin A) where A is the difference between the angular position for the at least one scintillation and the angular position of the collimating means.

36. The method as set forth in claim 33 further comprising the step of computing in electrical form sums of the outputs of units having the same axial position.

37. The method as set forth in claim 33 further comprising the step of computing in electrical form a position value for at least one of the scintillations substantially proportional to a weighted sum of the sums of the outputs of units having the same axial position divided by the sum of the axial sums.

38. The method as set forth in claim 37 further for use with collimating means having an angular position inside the tubular body, the method further comprising the step of computing in electrical form a second position value substantially proportional to (1−cos A+sin A) where A is the difference between the angular position for the at least one scintillation and the angular position of the collimating means.

39. The method as set forth in claim 33 further comprising the step of generating signals representing an axial position and a transverse position for the at least one scintillation.

40. The method as set forth in claim 39 further comprising the step of generating a tomographic display utilizing the signals representing axial position and transverse position for a plurality of the scintillations.

41. The method as set forth in claim 39 for use with a specimen emitting ionizing radiation from within the tubular body further comprising the step of producing at least one representation of the specimen utilizing the signals representing axial position and transverse position for a plurality of the scintillations.

42. The method as set forth in claim 39 further comprising the step of generating other signals representing another axial position and another transverse position to which a predetermined value has been added.

43. The method as set forth in claim 33 further comprising the preliminary steps of summing all of the outputs of the converting means occurring at any one time; comparing the sum so obtained with a predetermined range; and, only if the sum so obtained is within the range, producing imaging information corresponding to the outputs at that time.

44. Radiation imaging apparatus comprising:
a substantially tubular scintillation body with a longitudinal axis, the body being composed of a material for producing photon events in response to bombardment by ionizing radiation, each photon event having a position relative to each of first and second coordinate perpendicular to the axis;
means for converting first and second photon events, resulting in said scintillation body from pairs of ionizing photons emitted by a position annihilation event, to electrical outputs, the converting means includng rows of scintillation sensing units disposed around the outside of the tubular scintillation body; and
means for generating for each row a sum of the outputs of the units therein, for identifying the row having the largest sum and the row having the second largest sum, for generating a value for the first coordinate position perpendicular to the axis and a value for the second coordinate position, perpendicular to the axis, of the first photon event from the sum for the row with the largest sum and the sums for at least its two adjacent rows, and for generating a value for the first coordinate position perpendicular to the axis and a value for the second coordinate position, perpendicular to the axis, of the second photon event from the sum for the row with the second largest sum and the sums for at least its two adjacent rows.

45. Radiation imaging apparatus as set forth in claim 44 wherein the generating means comprises means for also generating a value of angular position for the first photon event from the values for the first and second coordinate positions of the first photon event and for generating a value of angular position for the second photon event from the values for the first and second coordinate positions of the second photon event.

46. Radiation imaging apparatus as set forth in claim 44 wherein the generating means comprises means for also generating a value of axial position for the first and second photon events from the outputs of the units comprised in the row with the largest sum and at least its two adjacent rows and a value of axial position for the second photon event from the outputs of the units comprised in the row with the second largest sum and at least its two adjacent rows.

47. Radiation imaging apparatus as set forth in claim 46 further comprising:
means responsive to the generating means for displaying an image derived from the values of the first and second coordinate positions and the axial positions for the first and second photon events for each of many instances of positron annihilation.

48. Radiation imaging apparatus as set forth in claim 46 wherein the generating means comprises means for also generating an angle value as a function of the values of the first and second coordinate positions generated for both the first and second photon events when the values of axial position of the first and second photon events are substantially equal.

49. Radiation imaging apparatus as set forth in claim 48 wherein the generating means comprises means for also generating a value of transverse position for the positron annihilation event as a function of the difference between the angle value and an angular position value for the first photon event, which angular position value is computed as a function of the first and second coordinate position values of the first photon event.

50. Radiation imaging apparatus as set forth in claim 49 wherein the generating means comprises means for also supplying as an output for the apparatus the value of the axial position of one of the photon events, the transverse position value and the angle value.

51. A radiation imaging method for use with a substantially tubular scintillation body with a longitudinal axis, the body being composed of a material for producing photon events in response to bombardment by ionizing radiation, each photon event having a position relative to each of first and second coordinates perpendicular to the axis, the method comprising the steps of:
converting first and second photon events, resulting in the scintillation body from pairs of ionizing photons emitted by a positron annihilation event, to electrical outputs by using rows of scintillation sensing units disposed around the outside of the tubular scintillation body;
generating for each row a sum of the outputs of the units therein;
identifying the row having the largest sum and the row having the second largest sum; and generating a value for the first coordinate position and a value for the second coordinate position of the first photon event from the sum for the row with the largest sum and the sums for at least its two adjacent rows, and generating a value for the first coordinate position and a value for the second coordinate position of the second photon event from the sum for the row with the second largest sum and the sums for at least its two adjacent rows.

52. The method as set forth in claim 51 further comprising the steps of generating a value of angular position for the first photon event from the values for the first and second coordinate positions of the first photon event and generating a value of angular position for the second photon event from the values for the first and second coordinate positions of the second photon event.

53. The method as set forth in claim 51 further comprising the steps of: generating a value of axial position for the first and second photon events from the outputs of the units comprised in the row with the largest sum and at least its two adjacent rows and a value of axial position for the second photon event from the outputs of the units comprised in the row with the second largest sum and at least its two adjacent rows.

54. The method as set forth in claim 53 further comprising the step of displaying an image derived from the values of the first and second coordinate positions and the axial positions for the first and second photon events for each of many instances of positron annihilation.

55. The method as set forth in claim 53 further comprising the step of generating an angle value as a function of the values of first and second photon events when the values of axial position of the first and second photon events are substantially equal.

56. The method as set forth in claim 55 further comprising the step of generating a value of transverse position for the positron annihilation event as a function of the difference between the angle value and an angular position value for the first photon event, which angular position value is computed as a function of the first and second coordinate position values of the first photon event.

57. A radiation imaging method for use with a substantially tubular body having an axis and composed of a material for producing scintillations in response to bombardment by ionizing radiation, the method comprising the steps of:

converting the scintillations to electrical outputs with a plurality of scintillation sensing units disposed both along and around the outside of the tubular body and having axial positions and positions relative to first and second coordinates perpendicular to the axis;

computing in electrical form a first weighted sum of the output of units, the output of each unit being weighted in the first weighted sum depending on its position relative to the first coordinate perpendicular to the tubular body axis;

computing in electrical form a second weighted sum of the outputs of the units, the output of each unit being weighted in the second weighted sum depending on its position relative to the second coordinate perpendicular to the tubular body axis; and computing in electrical form a value of position around the tubular body for at least one of the scintillations as a function of the first and second weighted sums for the first and second coordinates perpendicular to the tubular body axis.

58. The method as set forth in claim 57 wherein the position value computing step comprises computing in electrical form an angular position for at least one of the scintillations as the arctangent of the ratio of the weighted sums for the first and second coordinates.

59. The method as set forth in claim 57 wherein the position value computing step comprises computing in electrical form a transverse position for at least one of the scintillations as a function of the ratio of the weight sums for the first and second coordinates.

60. The method as set forth in claim 57 further for use with collimating means having an angular position wherein the position value computing step comprises computing in electrical form a transverse position for at least one of the scintillations substantially proportional to the function $(1 - \cos A + \sin A)$ where A is the difference between the arctangent of the ratio of the first and second weighted sums and the angular position of the collimating means.

61. The method as set forth in claim 57 wherein the position value computing step comprises computing in electrical form a transverse position for at least one of the scintillations substantially proportional to the sum of unity and the ratio of the difference of the first and second weighted sums to the square root of the sum of the squares of the first and second weighted sums.

62. The method as set forth in claim 57 wherein the position value computing step comprises computing in electrical form a transverse position for at least one of the scintillations substantially proportional to unity less the product of the square root of two with the ratio of the first weighted sum to the square root of the sum of the squares of the first and second weighted sums.

63. Radiation imaging apparatus comprising:
a tubular optically continuous body having an axis and circumference and producing scintillations in response to bombardment by ionizing radiation;
means for converting the scintillations to electrical outputs, including a plurality of scintillation sensing units disposed along and around said tubular body, said scintillation sensing units having respective positions relative to first and seocnd coordinates perpendicular to the axis of said tubular body; and
means for computing in electrical form a first weighted sum of the outputs of said scintillation sensing units weighted substantially in relationship to their first coordinate positions and a second weighted sum of the of the outputs of said scintillation sensing units weighted substantially in relationship to their second coordinate positions wherein the first and second weighted sums substantially represent respectively the first and second coordinate positions of at least one of the scintillations.

64. Radiation imaging apparatus as set forth in claim 63 further comprising collimating means inside said tubular body and having an angular position and means for generating a transverse position signal representing a value which is a function of both the first and seocnd weighted sums and the angular position of said collimating means relative to the tubular body.

65. Radiation imaging apparatus as set forth in claim 64 for use with a specimen emitting ionizing radiation inside said tubular body further comprising means responsive to the transverse position signal and the angular position of said collimating means relative to the specimen for producing a visual display of the specimen.

66. Radiation imaging apparatus as set forth in claim 65 further comprising means for supplying an electrical signal representative of the angular position of said collimating means directly to said means for producing the visual display and still further comprising switch means connected to said generating means for limting said generating means to at least one particular value of the angular position of said collimating means.

67. Radiation imaging apparatus for use with a substantially tubular body having an axis and composed of a material for producing scintillations in response to bombardment by ionizing radiation, and means for converting the scintillations to electrical outputs, including a plurality of scintillation sensing units forming rings and rows exterior to the tubular scintillation body, the radiation imaging apparatus comprising:
- first means for comptuing in electricla form respective row sums of the outputs of units for each of the rows around the tubular body, each of the rows of scintillation sensing units being parallel to the axis of the tubular body and having positions relative to first and second coordinates perpendicular to the axis of the tubular body, said first means also including means for computing in electrical form a first weighted sum of the row sums weighted substantially in relationship to their relative first coordinate positions and a second weighted sum of the row sums weighted substantially in relationship to their relative second coordinate positions wherein the first and second weighted sums substantially represent respectively the first and second coordinate positions of at least one of the scintillations; and
- second means for computing in electrical form a position value representing a position around the circumference of said tubular body for at least one of the scintillations as a function of said first and second weighted sums of the row sums.

68. Radiation imaging apparatus comprising:
- a substantially tubular body having an axis and producing scintillations in response to bombardment by ionziing radiation;
- means for converting the scintillations to electrical outputs, including a plurality of scintillation sensing units forming rings and rows exterior to the tubular scintillation body;
- first means for computing in electrical form respective row sums of the outputs of units for each of the rows around the tubular body, each of the rows of scintillation sensing units being parallel to the axis of the tubular body and having positions relative to first and second coordinates perpendicular to the axis of the tubular body, said first means also including means for computing in electrical form a first weighted sum of the row sums weighted substantially in relationship to their relative first coordinate positions and a second weighted sum of the row sums weighted substantially in relationship to their relative second coordinate positions; and
- second means for computing in electrical form a position value representing a position around the circumference of said tubular body for at least one of the scintillations as a function of said first and second weighted sums of the row sums.

69. Radiation imaging apparatus as set forth in claim 68 further comprising collimating means inside said tubular body and having an angular position and wherein said second means also includes means for generating a transverse position signal representing a value which is a function of both the position of the scintillation around the circumference and the angular position of said collimating means.

70. Radiation imaging apparatus comprising:
- a substantially tubular body having an axis and producing scintillations in response to bombardment by ionizing radiation;
- means for converting the scintillations to electrical outputs including a plurality of scintillation sensing units forming pairs of rows exterior to said tubular body parallel to its axis and having positions relative to first and second coordinates perpendicular to its axis so that every unit in a given particular pair of rows has the same first coordinate position and every unit in another given particular pair of rows has the same second coordinate position;
- means for producing respective first sum signals representing sums of the outputs of units in each of the particular pairs of rows having the same first coordinate position;
- means for producing respective second sum signals representing sums of the outputs of units in each of the particular pairs of rows having the same second coordinate positions; and
- means for producing as a function of the first sum signals a first electrical signal to represent a first coordinate position perpendicular to the tubular body axis of at least one of the scintillations, and for producing as a function of the second sum signals a second electrical signal to represent a second coordinate position perpendicular to the tubular body axis of the same one of the scintillations.

71. Radiation imaging apparatus as set forth in claim 70 further comprising means for generating a transverse position signal for the same one of the scintillations from the first and second electrical signals.

72. Radiation imaging apparatus comprising:
- a tubular body having an axis and producing scintillations in response to bombardment by ionizing radiation;
- means for converting the scintillations to electrical outputs including a plurality of scintillation sensing units disposed both along and around the outside of said tubular body and having positions relative to first and second coordinates perpendicular to the axis; and
- means for computing in electrical form a weighted sum of the sums of the outputs of units having the same position relative to the first coordinate, a weighted sum of the sums of the outputs of units having the same position relative to the second coordinate, and an angular position for at least one of the scintillations substantially as the arctangent of the ratio of the weighted sums for the first and second coordinates.

73. Radiation imaging apparatus as set forth in claim 72 wherein said computing means includes analog summing means for computing the weighted sums and digital computing means for computing the arctangent, said digital computing means being fed by said analog summing means.

74. Radiation imaging apparatus comprising:

a substantially optically continuous tubular body having an axis and producing scintillations in response to bombardment by ionizing radiation;

collimating means said tubular body and having an angular position;

means for converting the scintillations to electrical outputs including a plurality of scintillation sensing units disposed along and around the outside of said tubular body; and electronic means connected to the electrical outputs for generating a position signal representing a value substantially proportional to $(1-\cos A + \sin A)$ where A is the difference between an angular position of a scintillation and the angular position of said collimating means.

75. Radiation imaging apparatus as set forth in claim 74 for use with a specimen emitting ionizing radiation inside said tubular body and further comprising means for generating a display image of the specimen utilizing the position signal and the angular position of said collimating means relative to the specimen for each of a plurality of the scintillations.

76. Radiation imaging apparatus as set forth in claim 74 wherein said units have respective axial psitions along asid tubular body, and said electronic means further comprises means for producing a second position signal represneting a value substantially proportional to a weighted sum of the sums of the outputs of units having the same axial position divided by the sum of the axial sums.

77. Radiation imaging apparatus as set forth in claim 76 further comprising means connected to said electronic means for generating a display image utilizing the first-named position signal and the second position signal for each of a plurality of the scintillations.

78. Radiation imaging apparatus for use with a specimen emitting ionizing radiation, comprising:

a tubular body having an axis and producing scintillations in response to bombardment by the ionizing radiation;

collimating means providing a plurality of directions of collimation inside said tubular body;

means for converting the scintillations to electrical outputs including a plurality of scintillation sensing units disposed both along and around the outside of said tubular body;

electronic means for computing values of axial and transverse position for the scintillations; and means for producing a display in response to the computed values from said electronic means, said electronic means including means for adding at least one predetermined value to some of the values of axial position and transverse position to cause said display to show distinct views of the specimen as viewed along at least two of the directions of collimation.

79. Radiation imaging apparatus as set forth in claim 78 wherein said electronic means also includes means for computing angular positions of the scintillations in said tubular body and determining when to add the predetermined value to some of the values of axial and transverse position based on the angular positions.

80. Radiation imaging apparatus comprising:

a substantially tubular scintillation body with a longitudinal axis, the body being composed of a material for producing photon events in response to bombardment by ionizing radiation, each photon event having an axial position;

means for converting first and second photon events, resulting in said scintillation body from pairs of ionizing photons emitted by positron annihilation event, to electrical outputs, the converting means including scintillation sensing units disposed along and around the outside of the tubular scintillation body; and means responsive to the electrical outputs of said converting means for computing first and second values of axial position for the first and second photon events respectively and for generating a signal representing imaging information for the positron annihilation event only when the first and second values of axial position are substantially equal.

81. Radiation imaging apparatus as claimed in claim 80 for use with a specimen emitting ionizing radiation from positron annihilation events further comprising means responsive to the signal representing imaging information for visually displaying at least one representation of the specimen.

82. Radiation imaging apparatus as claimed in claim wherein the signal representing imaging information represents a value of transverse position.

83. Radiation imaging apparatus as claimed in claim 85 wherein the signal representing imaging information includes a value of transverse position, a value of axial position, and a value of an angle analogous to a collimator angle.

84. Radiation imaging apparatus as claimed in claim wherein said generating means includes means for producing the signal that represents imaging information to include a value of an angle analogous to a collimator angle by computing first and second values of angular position of the first and second photon events respectively, and supplying the analogous angle as a function of both a particular one of the angular position values and the magnitude of the difference of the angular position values.

85. Radiation imaging apparatus as claimed in claim 84 for use with a specimen emitting ionizing radiation from positron annihilation events, further comprising means responsive to the signal representing imaging information for visually displaying at least one representation of the specimen.

86. Radiation imaging apparatus as claimed in claim 85 wherein the signal representing imaging information also includes a value of axial position, and a value of transverse position.

87. Radiation imaging apparatus as claimed in claim 85 wherein the signal representing imaging information also includes a value of axial position, and a value of transverse position computed as a function of the difference of one of the angular position values and the analogous angle.

88. Radiation imaging apparatus comprising:

a tubular substantially optically continuous scintillation body with an axis, said tubular scintillation body being composed of a material for producing photon events in response to bombardment by ionizing radiation, each photon event having an angular position;

means for converting first and second photon events, resulting in said tubular scintillation body from pairs of ionizing photons emitted by a positron annihilation event, to electrical outputs, the converting means including a scintillation sensing units disposed along and around the outside of the tubular scintillation body; and means responsive to the electrical outputs of said converting means for generating a signal representing imaging information for the position annihilation event by computing first and second values of angular position of the first and second photon events respectively, and computing an angle analogous to a collimator angle as a function of both a particular one of the angular position values and the magnitude of the difference of the angular position values, the signal including the analogous angle value.

89. Radiation imaging apparatus as claimed in claim 88 wherein the scintillation sensing units form a number of rows and the rows correspond to row identification numbers and said generating means includes means for determining the row identification numbers of the rows with first and second largest sums of the electrical outputs of their units for each of a plurality of positron annihilation events and for preventing the signal from being generated for a particular positron annihilation event when the absolute value of the difference of the row identification numbers of the rows with the first and second largest sums is outside of a range between a predetermined first number and a second number, the second number being equal to the number of rows less the predetermined first number.

90. Radiation imaging apparatus as claimed in claim 88 for use with a specimen emitting ionizing radiation from positron annhiliation events further comprising means responsive to the signal representing imaging information for visually displaying at least one representation of the specimen.

91. Radiation imaging apparatus as claimed in claim 88 wherein said generating means also includes means for computing a value of transverse position as a function of the difference of one of the angular position values and the analogous angle, the signal also including the transverse position value.

92. Radiation imaging apparatus as claimed in claim 88 wherein said generating means also includes means for computing a value of transverse position substantially proportional to $(1-\cos A + \sin A)$ where A is the difference between one of the angular position values and the analogous angle, the signal also including the transverse position value.

* * * * *